(12) United States Patent
Ojard et al.

(10) Patent No.: US 12,216,741 B2
(45) Date of Patent: *Feb. 4, 2025

(54) INTER-CLUSTER INTENSITY VARIATION CORRECTION AND BASE CALLING

(71) Applicant: Illumina, Inc., San Diego, CA (US)

(72) Inventors: Eric Jon Ojard, San Francisco, CA (US); Abde Ali Hunaid Kagalwalla, San Diego, CA (US); Rami Mehio, San Diego, CA (US); Nitin Udpa, San Diego, CA (US); Gavin Derek Parnaby, Laguna Niguel, CA (US); John S. Vieceli, Encinitas, CA (US)

(73) Assignee: Illumina, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/501,904

(22) Filed: Nov. 3, 2023

(65) Prior Publication Data

US 2024/0220584 A1 Jul. 4, 2024

Related U.S. Application Data

(63) Continuation of application No. 18/154,603, filed on Jan. 13, 2023, now Pat. No. 11,853,396, which is a
(Continued)

(51) Int. Cl.
*G06T 7/33* (2017.01)
*G06F 18/2135* (2023.01)
(Continued)

(52) U.S. Cl.
CPC .... *G06F 18/2411* (2023.01); *G06F 18/21355* (2023.01); *G06T 7/187* (2017.01); *G06V 10/507* (2022.01)

(58) Field of Classification Search
CPC .......... G06T 7/187; G06T 5/00; G06V 10/50; G06V 10/762; G06V 10/82; G06V 20/69;
(Continued)

(56) References Cited

U.S. PATENT DOCUMENTS 6,598,013 B1   7/2003   Domnisoru et al.
6,778,692 B1   8/2004   Yazici
(Continued)

FOREIGN PATENT DOCUMENTS

EP   3306566 A1   4/2018
JP   2015501974 A   1/2015
(Continued)

OTHER PUBLICATIONS

Abbaszadegan, "An Encoder-Decoder Based Basecaller for Nanopore DNA Sequencing", dated Feb. 2019, 112 pgs.
(Continued)

*Primary Examiner* — Quan M Hua
(74) *Attorney, Agent, or Firm* — Keller Preece PLLC

(57) ABSTRACT

The technology disclosed corrects inter-cluster intensity profile variation for improved base calling on a cluster-by-cluster basis. The technology disclosed accesses current intensity data and historic intensity data of a target cluster, where the current intensity data is for a current sequencing cycle and the historic intensity data is for one or more preceding sequencing cycles. A first accumulated intensity correction parameter is determined by accumulating distribution intensities measured for the target cluster at the current and preceding sequencing cycles. A second accumulated intensity correction parameter is determined by accumulating intensity errors measured for the target cluster at the current and preceding sequencing cycles. Based on the first and second accumulated intensity correction parameters, next intensity data for a next sequencing cycle is
(Continued)

corrected to generate corrected next intensity data, which is used to base call the target cluster at the next sequencing cycle.

20 Claims, 15 Drawing Sheets

Related U.S. Application Data continuation of application No. 17/752,789, filed on May 24, 2022, now Pat. No. 11,593,595, which is a continuation of application No. 17/510,285, filed on Oct. 25, 2021, now Pat. No. 11,361,194.

(60) Provisional application No. 63/106,256, filed on Oct. 27, 2020.

(51) Int. Cl.
  *G06F 18/2411* (2023.01)
  *G06T 7/187* (2017.01)
  *G06V 10/50* (2022.01)

(58) Field of Classification Search
  CPC ............ G06V 10/94; G06N 3/08; G06N 3/04; G06N 3/0464; G06N 3/084; G06N 3/12; G16B 30/00; G16B 40/10; G16B 30/20; G16B 40/20; G16B 40/30; G16B 40/00; G16B 45/00; G01N 21/64; G01N 33/543; G01N 33/58; C12Q 1/6869; C12Q 1/6844; C12Q 1/6876; C12Q 1/68; C12Q 1/682; C12Q 1/6867
  See application file for complete search history.

(56) References Cited

U.S. PATENT DOCUMENTS

| | | | |
|---|---|---|---|
| 6,865,301 B1 | 3/2005 | Harris | |
| 10,068,053 B2 | 9/2018 | Kermani et al. | |
| 11,188,778 B1 | 11/2021 | Ojard et al. | |
| 11,361,194 B2 * | 6/2022 | Ojard | G16B 40/30 |
| 11,593,595 B2 * | 2/2023 | Ojard | G06T 7/187 |
| 11,853,396 B2 * | 12/2023 | Ojard | G06V 10/507 |
| 2002/0034337 A1 | 3/2002 | Shekter | |
| 2006/0020203 A1 | 1/2006 | Tamura | |
| 2007/0194249 A1 | 8/2007 | Gavrilov et al. | |
| 2009/0024331 A1 | 1/2009 | Tomaney et al. | |
| 2010/0034444 A1 | 2/2010 | Emhoff et al. | |
| 2010/0160172 A1 | 6/2010 | Erlich et al. | |
| 2011/0256631 A1 | 10/2011 | Tomaney et al. | |
| 2012/0015825 A1 | 1/2012 | Zhong et al. | |
| 2012/0020537 A1 | 1/2012 | Garcia et al. | |
| 2013/0109577 A1 | 5/2013 | Korlach et al. | |
| 2013/0110407 A1 | 5/2013 | Baccash et al. | |
| 2013/0184796 A1 | 7/2013 | Marzano et al. | |
| 2014/0221216 A1 | 8/2014 | Cope et al. | |
| 2015/0057167 A1 | 2/2015 | Kaiser et al. | |
| 2015/0065353 A1 | 3/2015 | Turner et al. | |
| 2015/0079596 A1 | 3/2015 | Eltoukhy et al. | |
| 2015/0169824 A1 | 6/2015 | Kermani et al. | |
| 2015/0337388 A1 | 11/2015 | Garner, Jr. et al. | |
| 2017/0003405 A1 | 1/2017 | Ahlen et al. | |
| 2017/0318240 A1 | 11/2017 | Yu | |
| 2018/0195953 A1 * | 7/2018 | Langlois | C12Q 1/6869 |
| 2018/0260940 A1 | 9/2018 | Langlois et al. | |
| 2018/0274023 A1 | 9/2018 | Belitz et al. | |
| 2020/0302224 A1 | 9/2020 | Jaganathan et al. | |
| 2020/0302297 A1 | 9/2020 | Jaganathan et al. | |
| 2020/0350037 A1 | 11/2020 | Mishra | |
| 2020/0364496 A1 | 11/2020 | Kostem | |
| 2020/0364565 A1 | 11/2020 | Kostem | |
| 2021/0118110 A1 | 4/2021 | Langlois et al. | |
| 2021/0310065 A1 * | 10/2021 | Belitz | G16B 30/00 |
| 2022/0067418 A1 | 3/2022 | Ojard et al. | |
| 2023/0268033 A1 * | 8/2023 | Jaganathan | G06V 10/454 |
| | | | 706/20 |

FOREIGN PATENT DOCUMENTS

| | | | |
|---|---|---|---|
| JP | 2017520821 A | | 7/2017 |
| KR | 20240047475 A | * | 9/2022 |
| WO | 0063437 A3 | | 1/2002 |
| WO | 2015/002813 A1 | | 1/2015 |
| WO | 2015/173222 A1 | | 11/2015 |
| WO | 2016/061396 A1 | | 4/2016 |
| WO | 2016/066586 A1 | | 5/2016 |
| WO | 2017/098013 A1 | | 6/2017 |
| WO | 2021/226285 A1 | | 11/2021 |
| WO | 2022/093865 A1 | | 5/2022 |

OTHER PUBLICATIONS

Boza et al., "DeepNano: Deep recurrent neural network for base calling in MinION nanopore reads", dated Jun. 5, 2017, 13 pages.
Dressman et al., "Transforming single DNA molecules into fluorescent magnetic particles for detection and enumeration of genetic variations", Proceedings of the National Academy of Science, vol. 100, No. 15, pp. 8817-8822, dated Jul. 22, 2003, 6 pages.
Genome Analysis Wiki, "Base Caller Summaries", date of last edit Mar. 12, 2010, 4 pages.
Huang et al., "SACal: a neural network basecaller for Oxford Nanopore sequencing data based on self-attention mechanism", dated 2020, 10 pages.
Kao et al., "BayesCall: A model-based base-calling algorithm for high-throughput short-read sequencing", 2009 Genome Research, vol. 19, pp. 1884-1895.
Kao et al., "naiveBayesCall: An Efficient Model-Based Base-Calling Algorithm for High-Throughput Sequencing", Research In Computational Molecular Biology, Springer Berlin Heidelberg, Berlin, Heidelberg, Apr. 25, 2010, pp. 233 247.
Kircher et al., "Improved base calling for the Illumina Genome Analyzer using machine learning strategies", dated Aug. 41, 2009, 9 pages.
Konishi et al., "Halcyon: an accurate basecaller exploiting an encoder-decoder model with monotonic attention", dated Nov. 9, 2020, 7 pages.
Massingham et al., "All your base: a fast and accurate probabilistic approach to base calling", Genome Biology, Biomed Central, Ltd. Vol 13, No. 2, Feb. 29, 2012, 15 pgs.
Miculinic et al., "MinCall—MinION end2end convolutional deep learning basecaller", dated Apr. 2, 2019, 8 pages.
Oxford, Cacho et al., "A comparison of Base-calling Algorithms for Illumina Sequencing Technology", dated Oct. 5, 2015, 10 pages.
Peresini et al., "Nanopore Base Calling on the Edge", dated Nov. 9, 2020, 15 pages.
Ratkovic, "Deep Learning Model for Base Calling of MinION Nanopore Reads", dated Mar. 3, 2017, 48 pages. (University of Zagreb).
Thornley et al., "Machine Learning in Basecalling—Decoding Trace Peak Behavior", dated Oct. 2006, 9 pages.
University of Cambridge, "Artificial Intelligence for genomic medicine", dated May 2020, 63 pages.
Wang et al., "WaveNano: a signal-level nanopore base caller simultaneous prediction of nucleotide labels and move labels through bi-directional WaveNets", dated 2018, 10 pages.
Wang Bo et al., "An adaptive decorrelation method removes Illumina DNA base-calling errors caused by crosstalk between adjacent clusters", Feb. 20, 2017, 11 pages.
Wick et al., "Performance of neural network basecalling tools for Oxford Nanopore sequencing", dated 2019, 10 pages.
Wikipedia, "Least Squares", 13 pages, retrieved on Mar. 7, 2022, retrieved from the internet [URL: https://en.wikipedia. prg/w/index.php?title=Least_squares&oldid=951737821].

(56) References Cited

OTHER PUBLICATIONS

Wikipedia, "Ordinary Least Squares", 16 pages, retrieved on Mar. 7, 2022, retrieved from the internet [URL: https://en.wikipedia.org/w/index.php?title=Ordinary_least_squares&oldid=951770366].

Xuan Lv et al., "An end-to-end Oxford Nanopore Basecaller Using Convolution-augmented Transformer", dated 2020. 6 pages.

Zeng et al., "Causalcall: Nanopore Basecalling Using a Temporal Convolutional Network", dated Jan. 20, 2020, 11 pages.

* cited by examiner

Preceding Sequencing Cycle i - 1

Preceding accumulated intensity correction parameters for the target cluster 702

Current Sequencing Cycle i

Current measured intensity for the target cluster 712

Current base call for the target cluster 722

Next Sequencing Cycle i + 1

Current intensity correction parameters for the target cluster 732

734

Current accumulated intensity correction parameters for the target cluster 742

Current amplification coefficient for the target cluster 752

Current channel-specific offset coefficients for the target cluster 762

Next measured intensity for the target cluster 772

Next corrected measured intensity for the target cluster 782

Next base call for the target cluster 792

Subsequent Sequencing Cycle i + 2

784

Next intensity correction parameters for the target cluster 794

Next accumulated intensity correction parameters for the target cluster 796

Next amplification coefficient for the target cluster 798

Next offset coefficients for the target cluster 799

Figure 7

If $a, d_1, d_2$, and $n_{c,i}$ have prior probability distributions $a \sim \mathcal{N}(1, \sigma_a^2)$, $d_1 \sim \mathcal{N}(0, \sigma_{d_1}^2)$, $d_2 \sim \mathcal{N}(0, \sigma_{d_2}^2)$, $n_{c,i} \sim \mathcal{N}(0, \sigma_n^2)$, then we can find the maximum likelihood solution: — 902

Let $e_{c,i} = y_{c,i} - x_{c,i}$ $$\bar{x}_1 \triangleq \frac{1}{C}\sum_{c=1}^{C} x_{c,1} \quad \bar{x}_2 \triangleq \frac{1}{C}\sum_{c=1}^{C} x_{c,2} \quad \overline{xx} \triangleq \frac{1}{C}\sum_{c=1}^{C}(x_{c,1}^2 + x_{c,2}^2)$$

$$\bar{e}_1 \triangleq \frac{1}{C}\sum_{c=1}^{C} e_{c,1} \quad \bar{e}_2 \triangleq \frac{1}{C}\sum_{c=1}^{C} e_{c,2} \quad \overline{xe} \triangleq \frac{1}{C}\sum_{c=1}^{C}(x_{c,1}e_{c,1} + x_{c,2}e_{c,2})$$
— 904

$$k_a(C) = \frac{\sigma_n^2}{C\sigma_a^2}, \quad k_{d_1}(C) = \frac{C\sigma_{d_1}^2}{C\sigma_{d_1}^2 + \sigma_n^2}, \quad k_{d_2}(C) = \frac{C\sigma_{d_2}^2}{C\sigma_{d_2}^2 + \sigma_n^2}$$
— 906, 908, 910

$$\hat{a} = 1 + \frac{\overline{xe} - \bar{x}_1\bar{e}_1k_{d_1}(C) - \bar{x}_2\bar{e}_2k_{d_2}(C)}{\overline{xx} + k_a(C) - \bar{x}_1^2 k_{d_1}(C) - \bar{x}_2^2 k_{d_2}(C)}$$
— 920

$$\hat{d}_1 = (\bar{e}_1 + \bar{x}_1(1-\hat{a}))k_{d_1}(C)$$ — 930

$$\hat{d}_2 = (\bar{e}_2 + \bar{x}_2(1-\hat{a}))k_{d_2}(C)$$ — 940

As $C \to \infty$, this approaches the least-squares solution

1002
1004 — if stats.cycle < tau
1006 —   decay_factor = 1.0;
         stats.cycle = stats.cycle + 1;
1008 — else
         decay_factor = 1 - 1 / tau;
       end 1010 — stats.xx_sum = decay_factor * stats.xx_sum + channel1(x).^2 + channel2(x).^2;
1012 — stats.x1_sum = decay_factor * stats.x1_sum + channel1(x);
1014 — stats.x2_sum = decay_factor * stats.x2_sum + channel2(x);

1016 — stats.xe_sum = decay_factor * stats.xe_sum + channel1(x) .* channel1(e) + channel2(x) .*channel2(e);
1018 — stats.e1_sum = decay_factor * stats.e1_sum + channel1(e);
1020 — stats.e2_sum = decay_factor * stats.e2_sum + channel2(e);

Figure 10

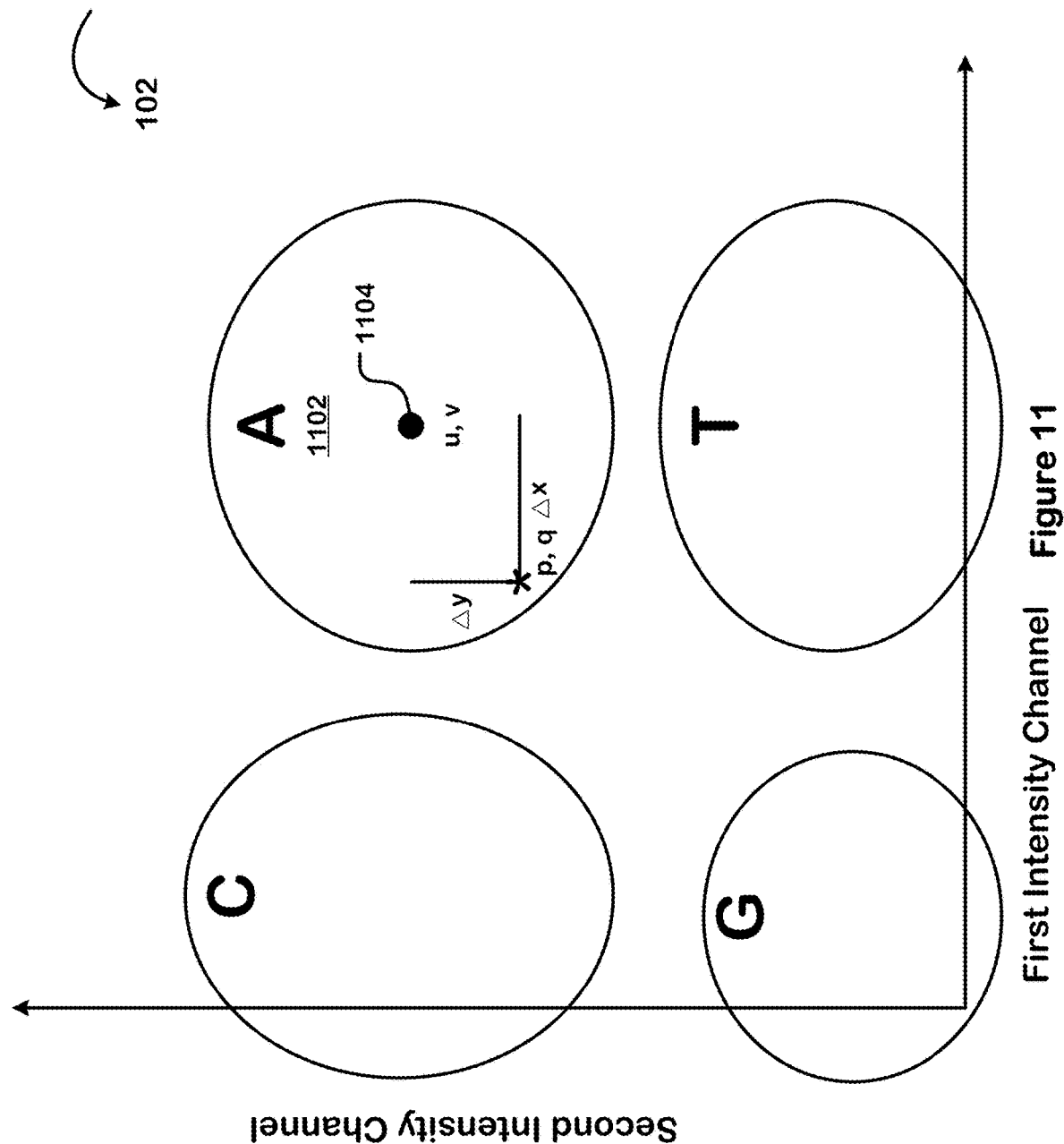

INTER-CLUSTER INTENSITY VARIATION CORRECTION AND BASE CALLING

PRIORITY APPLICATION

This application is a continuation of U.S. Nonprovisional patent application Ser. No. 18/154,603, entitled "INTER-CLUSTER INTENSITY VARIATION CORRECTION AND BASE CALLING," filed Jan. 13, 2023, which is a continuation of U.S. Nonprovisional patent application Ser. No. 17/752,789, entitled "INTER-CLUSTER INTENSITY VARIATION CORRECTION AND BASE CALLING," filed May 24, 2022, which is a continuation of U.S. Nonprovisional patent application Ser. No. 17/510,285, entitled "SYSTEMS AND METHODS FOR PER-CLUSTER INTENSITY CORRECTION AND BASE CALLING," filed Oct. 25, 2021, which in turn claims the benefit of U.S. Provisional Patent Application No. 63/106,256, entitled "SYSTEMS AND METHODS FOR PER-CLUSTER INTENSITY CORRECTION AND BASE CALLING," filed Oct. 27, 2020. The foregoing applications are incorporated by reference for all purposes.

STATEMENT OF COMMON OWNERSHIP

Pursuant to 35 USC § 102(b)(2)(C) and MPEP § 2146.02 (I), Applicant hereby states that this application and U.S. Provisional Patent Application No. 63/106,256, not later than the effective filing date of this application, were owned by or subject to an obligation of assignment to the same person (Illumina, Inc.), and that Illumina Software, Inc. is a wholly owned subsidiary of Illumina, Inc.

FIELD OF THE TECHNOLOGY DISCLOSED

The technology disclosed relates to apparatus and corresponding methods for the automated analysis of an image or recognition of a pattern. Included herein are systems that transform an image for the purpose of (a) enhancing its visual quality prior to recognition, (b) locating and registering the image relative to a sensor or stored prototype, or reducing the amount of image data by discarding irrelevant data, and (c) measuring significant characteristics of the image. In particular, the technology disclosed relates to generating variation correction coefficients to correct inter-cluster intensity profile variation in image data.

INCORPORATIONS

U.S. Provisional Patent Application No. 63/020,449, entitled, "EQUALIZATION-BASED IMAGE PROCESSING AND SPATIAL CROSSTALK ATTENUATOR," filed May 5, 2020;

U.S. Nonprovisional patent application Ser. No. 15/936,365, entitled "DETECTION APPARATUS HAVING A MICROFLUOROMETER, A FLUIDIC SYSTEM, AND A FLOW CELL LATCH CLAMP MODULE," filed on Mar. 26, 2018;

U.S. Nonprovisional patent application Ser. No. 16/567,224, entitled "FLOW CELLS AND METHODS RELATED TO SAME," filed on Sep. 11, 2019;

U.S. Nonprovisional patent application Ser. No. 16/439,635, entitled "DEVICE FOR LUMINESCENT IMAGING," filed on Jun. 12, 2019;

U.S. Nonprovisional patent application Ser. No. 15/594,413, entitled "INTEGRATED OPTOELECTRONIC READ HEAD AND FLUIDIC CARTRIDGE USEFUL FOR NUCLEIC ACID SEQUENCING," filed on May 12, 2017;

U.S. Nonprovisional patent application Ser. No. 16/351,193, entitled "ILLUMINATION FOR FLUORESCENCE IMAGING USING OBJECTIVE LENS," filed on Mar. 12, 2019;

U.S. Nonprovisional patent application Ser. No. 12/638,770, entitled "DYNAMIC AUTOFOCUS METHOD AND SYSTEM FOR ASSAY IMAGER," filed on Dec. 15, 2009;

U.S. Nonprovisional patent application Ser. No. 13/783,043, entitled "KINETIC EXCLUSION AMPLIFICATION OF NUCLEIC ACID LIBRARIES," filed on Mar. 1, 2013;

U.S. Nonprovisional patent application Ser. No. 13/006,206, entitled "DATA PROCESSING SYSTEM AND METHODS," filed on Jan. 13, 2011;

U.S. Nonprovisional patent application Ser. No. 14/530,299, entitled "IMAGE ANALYSIS USEFUL FOR PATTERNED OBJECTS," filed on Oct. 31, 2014;

U.S. Nonprovisional patent application Ser. No. 15/153,953, entitled "METHODS AND SYSTEMS FOR ANALYZING IMAGE DATA," filed on Dec. 3, 2014;

U.S. Nonprovisional patent application Ser. No. 14/020,570, entitled "CENTROID MARKERS FOR IMAGE ANALYSIS OF HIGH DENSITY CLUSTERS IN COMPLEX POLYNUCLEOTIDE SEQUENCING," filed on Sep. 6, 2013;

U.S. Nonprovisional patent application Ser. No. 14/530,299, entitled "IMAGE ANALYSIS USEFUL FOR PATTERNED OBJECTS," filed on Oct. 31, 2014;

U.S. Nonprovisional patent application Ser. No. 12/565,341, entitled "METHOD AND SYSTEM FOR DETERMINING THE ACCURACY OF DNA BASE IDENTIFICATIONS," filed on Sep. 23, 2009;

U.S. Nonprovisional patent application Ser. No. 12/295,337, entitled "SYSTEMS AND DEVICES FOR SEQUENCE BY SYNTHESIS ANALYSIS," filed on Mar. 30, 2007;

U.S. Nonprovisional patent application Ser. No. 12/020,739, entitled "IMAGE DATA EFFICIENT GENETIC SEQUENCING METHOD AND SYSTEM," filed on Jan. 28, 2008;

U.S. Nonprovisional patent application Ser. No. 13/833,619, entitled "BIOSENSORS FOR BIOLOGICAL OR CHEMICAL ANALYSIS AND SYSTEMS AND METHODS FOR SAME," filed on Mar. 15, 2013;

U.S. Nonprovisional patent application Ser. No. 15/175,489, entitled "BIOSENSORS FOR BIOLOGICAL OR CHEMICAL ANALYSIS AND METHODS OF MANUFACTURING THE SAME," filed on Jun. 7, 2016;

U.S. Nonprovisional patent application Ser. No. 13/882,088, entitled "MICRODEVICES AND BIOSENSOR CARTRIDGES FOR BIOLOGICAL OR CHEMICAL ANALYSIS AND SYSTEMS AND METHODS FOR THE SAME," filed on Apr. 26, 2013;

U.S. Nonprovisional patent application Ser. No. 13/624,200, entitled "METHODS AND COMPOSITIONS FOR NUCLEIC ACID SEQUENCING," filed on Sep. 21, 2012;

U.S. Provisional Patent Application No. 62/821,602, entitled "TRAINING DATA GENERATION FOR ARTIFICIAL INTELLIGENCE-BASED SEQUENCING," filed 21 Mar. 2019;

U.S. Provisional Patent Application No. 62/821,618, entitled "ARTIFICIAL INTELLIGENCE-BASED GENERATION OF SEQUENCING METADATA," filed 21 Mar. 2019;

U.S. Provisional Patent Application No. 62/821,681, entitled "ARTIFICIAL INTELLIGENCE-BASED BASE CALLING," filed 21 Mar. 2019;

U.S. Provisional Patent Application No. 62/821,724, entitled "ARTIFICIAL INTELLIGENCE-BASED QUALITY SCORING," filed 21 Mar. 2019;

U.S. Provisional Patent Application No. 62/821,766, entitled "ARTIFICIAL INTELLIGENCE-BASED SEQUENCING," filed 21 Mar. 2019;

NL Application No. 2023310, entitled "TRAINING DATA GENERATION FOR ARTIFICIAL INTELLIGENCE-BASED SEQUENCING," filed 14 Jun. 2019;

NL Application No. 2023311, entitled "ARTIFICIAL INTELLIGENCE-BASED GENERATION OF SEQUENCING METADATA," filed 14 Jun. 2019;

NL Application No. 2023312, entitled "ARTIFICIAL INTELLIGENCE-BASED BASE CALLING," filed 14 Jun. 2019;

NL Application No. 2023314, entitled "ARTIFICIAL INTELLIGENCE-BASED QUALITY SCORING," filed 14 Jun. 2019; and NL Application No. 2023316, entitled "ARTIFICIAL INTELLIGENCE-BASED SEQUENCING," filed 14 Jun. 2019.

U.S. Nonprovisional patent application Ser. No. 16/825,987, entitled "TRAINING DATA GENERATION FOR ARTIFICIAL INTELLIGENCE-BASED SEQUENCING," filed 20 Mar. 2020;

U.S. Nonprovisional patent application Ser. No. 16/825,991 entitled "TRAINING DATA GENERATION FOR ARTIFICIAL INTELLIGENCE-BASED SEQUENCING," filed 20 Mar. 2020;

U.S. Nonprovisional patent application Ser. No. 16/826,126, entitled "ARTIFICIAL INTELLIGENCE-BASED BASE CALLING," filed 20 Mar. 2020;

U.S. Nonprovisional patent application Ser. No. 16/826,134, entitled "ARTIFICIAL INTELLIGENCE-BASED QUALITY SCORING," filed 20 Mar. 2020;

U.S. Nonprovisional patent application Ser. No. 16/826,168, entitled "ARTIFICIAL INTELLIGENCE-BASED SEQUENCING," filed 21 Mar. 2020;

U.S. Provisional Patent Application No. 62/849,091, entitled, "SYSTEMS AND DEVICES FOR CHARACTERIZATION AND PERFORMANCE ANALYSIS OF PIXEL-BASED SEQUENCING," filed May 16, 2019;

U.S. Provisional Patent Application No. 62/849,132, entitled, "BASE CALLING USING CONVOLUTIONS," filed May 16, 2019;

U.S. Provisional Patent Application No. 62/849,133, entitled, "BASE CALLING USING COMPACT CONVOLUTIONS," filed May 16, 2019;

U.S. Provisional Patent Application No. 62/979,384, entitled, "ARTIFICIAL INTELLIGENCE-BASED BASE CALLING OF INDEX SEQUENCES," filed Feb. 20, 2020;

U.S. Provisional Patent Application No. 62/979,414, entitled, "ARTIFICIAL INTELLIGENCE-BASED MANY-TO-MANY BASE CALLING," filed Feb. 20, 2020;

U.S. Provisional Patent Application No. 62/979,385, entitled, "KNOWLEDGE DISTILLATION-BASED COMPRESSION OF ARTIFICIAL INTELLIGENCE-BASED BASE CALLER," filed Feb. 20, 2020;

U.S. Provisional Patent Application No. 62/979,412, entitled, "MULTI-CYCLE CLUSTER BASED REAL TIME ANALYSIS SYSTEM," filed Feb. 20, 2020;

U.S. Provisional Patent Application No. 62/979,411, entitled, "DATA COMPRESSION FOR ARTIFICIAL INTELLIGENCE-BASED BASE CALLING," filed Feb. 20, 2020; and U.S. Provisional Patent Application No. 62/979,399, entitled, "SQUEEZING LAYER FOR ARTIFICIAL INTELLIGENCE-BASED BASE CALLING," filed Feb. 20, 2020.

BACKGROUND

The subject matter discussed in this section should not be assumed to be prior art merely as a result of its mention in this section. Similarly, a problem mentioned in this section or associated with the subject matter provided as background should not be assumed to have been previously recognized in the prior art. The subject matter in this section merely represents different approaches, which in and of themselves can also correspond to implementations of the claimed technology.

This disclosure relates to analyzing image data to base call clusters during a sequencing run. One challenge with the analysis of image data is variation in intensity profiles of clusters in a cluster population being base called. This causes a drop in data throughput and an increase in error rate during the sequencing run.

There are many potential reasons for the inter-cluster intensity profile variation. It may result from differences in cluster brightness, caused by fragment length distribution in the cluster population. It may result from phase error, which occurs when a molecule in a cluster does not incorporate a nucleotide in some sequencing cycle and lags behind other molecules, or when a molecule incorporates more than one nucleotide in a single sequencing cycle. It may result from fading, i.e., an exponential decay in signal intensity of clusters as a function of sequencing cycle number due to excessive washing and laser exposure as the sequencing run progresses. It may result from underdeveloped cluster colonies, i.e., small cluster sizes that produce empty or partially filled wells on a patterned flow cell. It may result from overlapping cluster colonies caused by unexclusive amplification. It may result from under-illumination or uneven-illumination, for example, due to clusters being located on edges of a flow cell. It may result from impurities on a flow cell that obfuscate emitted signal. It may result from polyclonal clusters, i.e., when multiple clusters are deposited in the same well.

An opportunity arises to correct the inter-cluster intensity profile variation. Improved base calling throughput and reduced base calling error rate during the sequencing run may result.

BRIEF DESCRIPTION OF THE DRAWINGS

FIG. 7 depicts another example of a base calling pipeline that implements the variation correction logic.

FIG. 9 shows one implementation of directly applying maximum likelihood weights to the variation correction coefficients.

FIG. 10 shows one implementation of applying an exponential decay factor to the variation correction coefficients.

FIG. 11 shows another implementation of determining channel-specific offset coefficients.

DETAILED DESCRIPTION

The following discussion is presented to enable any person skilled in the art to make and use the technology disclosed and is provided in the context of a particular application and its requirements. Various modifications to the disclosed implementations will be readily apparent to those skilled in the art, and the general principles defined herein may be applied to other implementations and applications without departing from the spirit and scope of the technology disclosed. Thus, the technology disclosed is not intended to be limited to the implementations shown but is to be accorded the widest scope consistent with the principles and features disclosed herein.

INTRODUCTION

Development of the technology disclosed began with the analysis of intensity profiles of clusters in a cluster population being base called during a sequencing run. Analysis revealed that the intensity profiles of the clusters in the cluster population take similar form (e.g., trapezoids), but differ in scale and shifts from an origin 132 of a multi-dimensional space 100. We refer to this as "inter-cluster intensity profile variation." The multi-dimensional space 100 can be a cartesian space, a polar space, a cylindrical space, or a spherical space.

Figure 1:
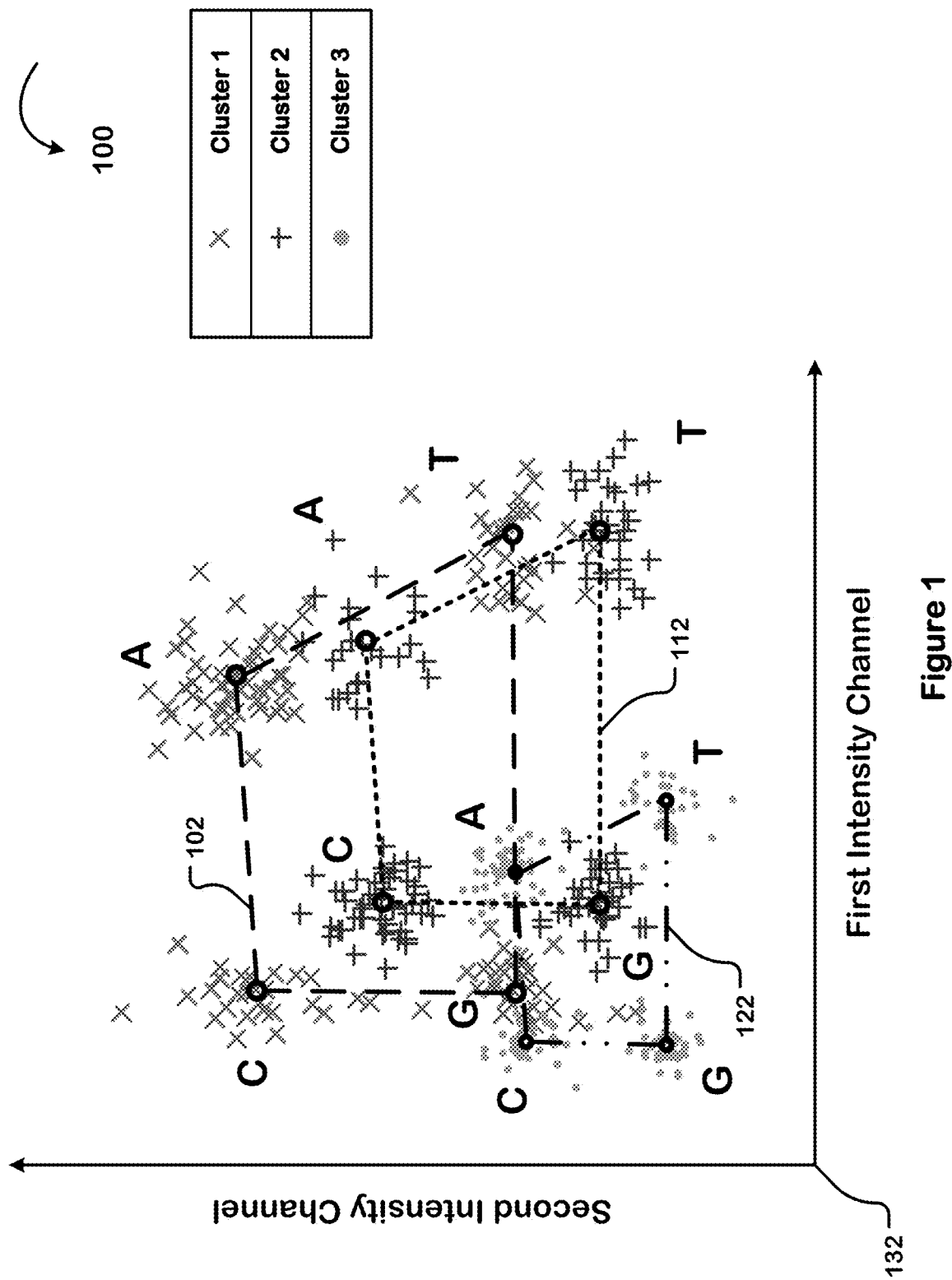
FIG. 1 illustrates one example of the inter-cluster intensity profile variation discovered and corrected by the technology disclosed.

FIG. 1 illustrates one example of the inter-cluster intensity profile variation discovered and corrected by the technology disclosed. FIG. 1 depicts intensity profiles 112, 122, and 132 of clusters 1, 2, and 3 in a cluster population, respectively. Intensity profile of a target cluster comprises intensity values that capture the chemiluminescent signals produced due to nucleotide incorporations in the target cluster at a plurality of sequencing cycles (e.g., 150) of the sequencing run.

In the implementation illustrated in FIG. 1, the intensity values are extracted from two different color/intensity channel sequencing images generated by a sequencer at each sequencing cycle in the plurality of sequencing cycles. Examples of the sequencer include Illumina's iSeq, HiSeqX, HiSeq 3000, HiSeq 4000, HiSeq 2500, NovaSeq 6000, NextSeq 550, NextSeq 1000, NextSeq 2000, NextSeqDx, MiSeq, and MiSeqDx.

In one implementation, the sequencer uses sequencing by synthesis (SBS) for generating the sequencing images. SBS relies on growing nascent strands complementary to cluster strands with fluorescently-labeled nucleotides, while tracking the emitted signal of each newly added nucleotide. The fluorescently-labeled nucleotides have a 3' removable block that anchors a fluorophore signal of the nucleotide type. SBS occurs in repetitive sequencing cycles, each comprising three steps: (a) extension of a nascent strand by adding the fluorescently-labeled nucleotide; (b) excitation of the fluorophore using one or more lasers of an optical system of the sequencer and imaging through different filters of the optical system, yielding the sequencing images; and (c) cleavage of the fluorophore and removal of the 3' block in preparation for the next sequencing cycle. Incorporation and imaging are repeated up to a designated number of sequencing cycles, defining the read length. Using this approach, each sequencing cycle interrogates a new position along the cluster strands.

In FIG. 1, the "✗" symbol represents the intensity values for cluster 1, the "✚" symbol represents the intensity values for cluster 2, and the "●" symbol represents the intensity values for cluster 3. The identity of the four different nucleotide types/bases A, C, T, and G is encoded as a combination of the intensity values in the two color images, i.e., the first and second intensity channels. For example, a nucleic acid can be sequenced by providing a first nucleotide type (e.g., base T) that is detected in the first intensity channel (x-axis of the multi-dimensional space 100), a second nucleotide type (e.g., base C) that is detected in the second intensity channel (y-axis of the multi-dimensional space 100), a third nucleotide type (e.g., base A) that is detected in both the first and the second intensity channels, and a fourth nucleotide type (e.g., base G) that lacks a label that is not, or minimally, detected in either intensity channels.

In some implementations, the intensity profile is generated by iteratively fitting four intensity distributions (e.g., Gaussian distributions) to the intensity values in the first and the second intensity channels. The four intensity distributions correspond to the four bases A, C, T, and G. In the intensity profile, the intensity values in the first intensity channel are plotted against the intensity values in the second intensity channel (e.g., as a scatterplot), and the intensity values segregate into the four intensity distributions.

The intensity profiles can take any shape (e.g., trapezoids, squares, rectangles, rhombus, etc.). Additional details about how the four intensity distributions are fitted to the intensity values for base calling can be found in U.S. Patent Application Publication No. 2018/0274023 A1, the disclosure of which is incorporated herein by reference in its entirety.

In one implementation, each intensity channel corresponds to one of a plurality of filter wavelength bands used by the optical system. In another implementation, each intensity channel corresponds to one of a plurality of imaging events at a sequencing cycle. In yet another implementation, each intensity channel corresponds to a combination of illumination with a specific laser and imaging through a specific optical filter of the optical system.

It would be apparent to one skilled in the art that the technology disclosed can be analogously applied to sequencing images generated using one-channel implementation, four-channel implementation, and so on. For example, in the case of four-channel implementation, four channel-specific offset coefficients are determined to correct shift variations in four intensity channels, respectively.

Variation Correction Logic

The inter-cluster intensity profile variation among intensity profiles of a large number (e.g., thousands, millions, billions, etc.) of clusters in the cluster population causes a drop in base calling throughput and an increase in base calling error rate. To correct the inter-cluster intensity profile variation, we disclose a variation correction logic that generates variation correction coefficients on a cluster-by-cluster basis.

In the two-channel implementation, the variation correction coefficients comprise an amplification coefficient that accounts for scale variation in the inter-cluster intensity profile variation, and two channel-specific offset coefficients that account for shift variation along the first and the second intensity channels in the inter-cluster intensity profile variation, respectively. In another implementation, the shift variation is accounted for by using a common offset coefficient for the different intensity channels (e.g., the first and the second intensity channels).

The variation correction coefficients for the target cluster are generated at a current sequencing cycle of the sequencing run based on combining analysis of historic intensity statistics determined for the target cluster at preceding sequencing cycles of the sequencing run with analysis of current intensity statistics determined for the target cluster at the current sequencing cycle. The variation correction coefficients are used to correct next intensity readings registered for the target cluster a next sequencing cycle of the sequencing run. The corrected next intensity readings are used to base call the target cluster at the next sequencing cycle. The result of repeatedly applying respective variation correction coefficients to respective intensity profiles of respective clusters at successive sequencing cycles of the sequencing run is that the intensity profiles become coincidental and anchored to the origin 132 (e.g., at the bottom lower corner of the trapezoids).

Figure 2:
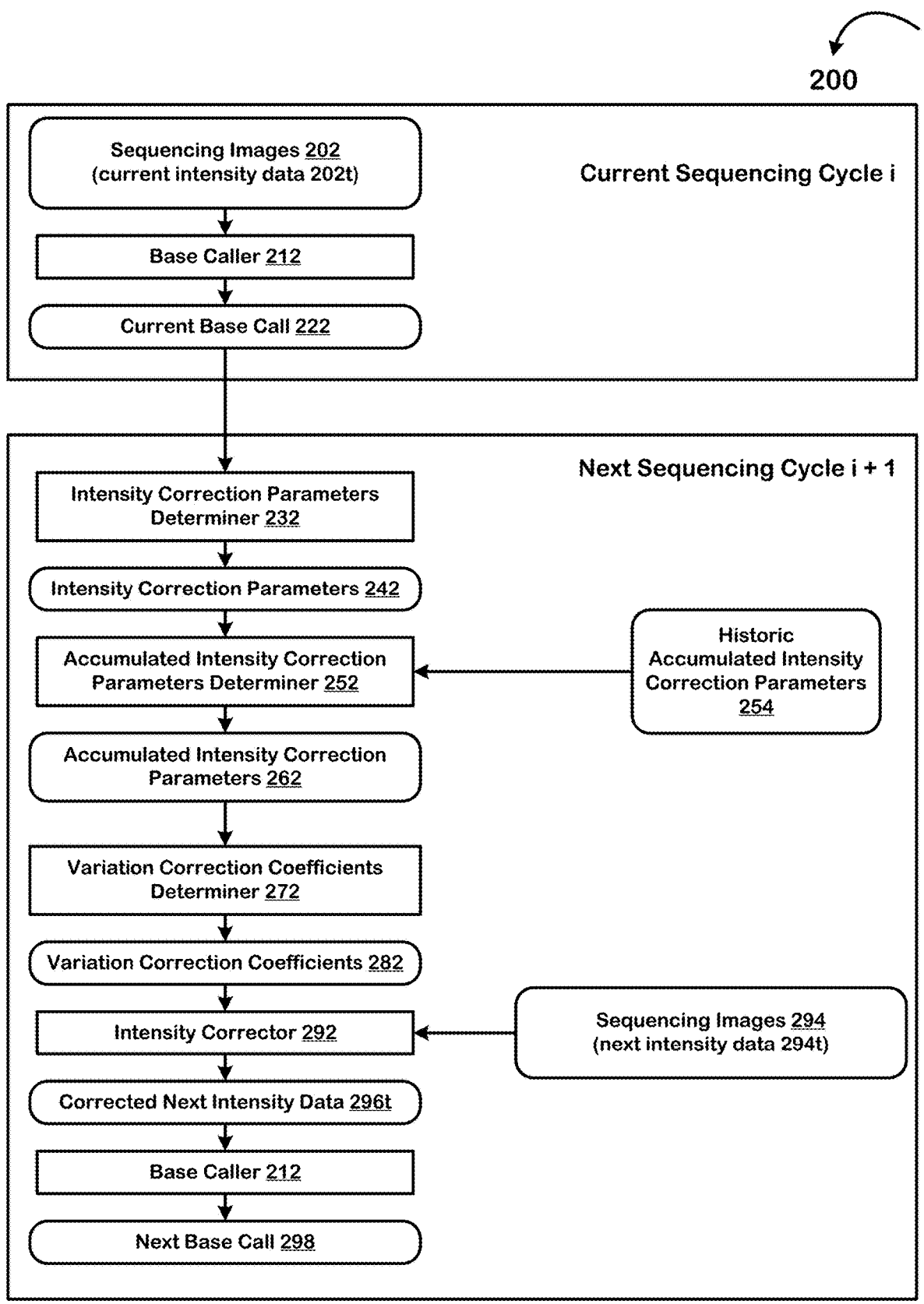
FIG. 2 illustrates an example of a base calling pipeline that implements the variation correction logic disclosed herein.

FIG. 2 illustrates an example of a base calling pipeline 200 that implements the variation correction logic.

Current Sequencing Cycle

At the current sequencing cycle i, the sequencer generates sequencing images 202. The sequencing images 202 contain current intensity data 202t registered for the target cluster at the current sequencing cycle i, along with containing current intensity data 202 registered for multiple clusters in the cluster population. The "t" in the current intensity data 202t refers to the target cluster.

The current intensity data 202t is provided to a base caller 212. The base caller 212 processes the current intensity data 202t and generates a current base call 222 for the target cluster at the current sequencing cycle i. Examples of the base caller 212 include Illumina's Real-Time Analysis (RTA) software, Illumina's neural network-based base caller (e.g., described in US Patent Publication No. US 2020/0302297 A1), and Illumina's equalizer-based base caller (e.g., described in U.S. Provisional Patent Application No. 63/020,449).

At the current sequencing cycle i, the intensity profile of the target cluster includes the current intensity data 202t, and current historic intensity data registered for the target cluster at those sequencing cycles of the sequencing run that precede the current sequencing cycle i, i.e., preceding sequencing cycles 1 to i−1. We collectively refer to the current intensity data 202t and the current historic intensity data as current available intensity data.

In the intensity profile, the four intensity distributions correspond to the four bases A, C, T, and G. In one implementation, the current base call 222 is made by determining which of the four intensity distributions the current intensity data 202t belongs to. In some implementations, this is accomplished by using an expectation maximization algorithm. The expectation maximization algorithm iteratively maximizes the likelihood of observing means (centroids) and distributions (covariances) that best fit the current available intensity data.

Once the four intensity distributions are determined at the current sequencing cycle i by using the expectation maximization algorithm, the likelihoods of the current intensity data 202t belonging to each of the four intensity distributions are calculated. The greatest likelihood gives the current base call 222. As an example, consider that "m, n" are the intensity values of the current intensity data 202t in the first and second intensity channels, respectively. The expectation maximization algorithm generates four values that represent the likelihoods of the "m, n" intensity values belonging to each of the four intensity distributions. The maximum of the four values identifies the called base.

In other implementations, a k-means clustering algorithm, a k-means-like clustering algorithm, a histogram based method, and the like can be used for base calling.

Next Sequencing Cycle

At the next sequencing cycle i+1, an intensity correction parameters determiner 232 determines intensity correction parameters 242 for the target cluster based on the current base call 222. In the two-channel implementation, the intensity correction parameters 242 include distribution intensity in the first intensity channel, distribution intensity in the second intensity channel, intensity error in the first intensity channel, intensity error in the second intensity channel, distribution centroid-to-origin distance, and distribution intensity-to-intensity error similarity measure.

We define each of the intensity correction parameters 242 as follows:

1) A distribution intensity in the first intensity channel is the intensity value in the first intensity channel at a centroid of a base-specific intensity distribution to which the target cluster belongs at the current sequencing cycle i. Note that the base-specific intensity distribution is the basis for calling the current base call 222.
2) A distribution intensity in the second intensity channel is the intensity value in the second intensity channel at the centroid of the base-specific intensity distribution.
3) An intensity error in the first intensity channel is the difference between the measured intensity value of the current intensity data 202t in the first intensity channel and the distribution intensity in the first intensity channel.
4) An intensity error in the second intensity channel is the difference between the measured intensity value of the current intensity data 202t in the second intensity channel and the distribution intensity in the second intensity channel.
5) A distribution centroid-to-origin distance is the Euclidean distance between the centroid of the base-specific intensity distribution and the origin 132 of the multi-dimensional space 100 in which the base-specific intensity distribution was fitted (e.g., by using the expectation maximization algorithm). In other implementations, distance metrics such as the Mahalanobis distance and the minimum covariance determinant (MCD) distances, and their associated centroid estimators can be used.
6) A distribution intensity-to-intensity error similarity measure is the summation of channel-wise dot products between the distribution intensities and the intensity errors in the first and second intensity channels.

An accumulated intensity correction parameter determiner 252 accumulates the intensity correction parameters 242 with historic accumulated intensity correction parameters 254 from preceding sequencing cycle i−1 to determine accumulated intensity correction parameters 262. Examples of accumulation include summing and averaging.

A variation correction coefficients determiner 272 determines variation correction coefficients 282 based on the determine accumulated intensity correction parameters 262.

At the next sequencing cycle i+1, the sequencer generates sequencing images 294. The sequencing images 294 contain next intensity data 294t registered for the target cluster at the next sequencing cycle i+1, along with containing next intensity data 294 registered for multiple clusters in the cluster population. The "t" in the next intensity data 294t refers to the target cluster.

An intensity corrector 292 applies the variation correction coefficients 282 to the next intensity data 294t to generate corrected next intensity data 296t. The "t" in the corrected next intensity data 296t refers to the target cluster.

At the next sequencing cycle i+1, the intensity profile of the target cluster includes the corrected next intensity data 296t, and next historic intensity data registered for the target cluster at those sequencing cycles of the sequencing run that precede the next sequencing cycle i+1, i.e., preceding sequencing cycles 1 to i. We collectively refer to the corrected next intensity data 296t and the next historic intensity data as next available intensity data.

The corrected next intensity data 296t is provided to the base caller 212. The base caller 212 processes the corrected next intensity data 296t and generates a next base call 298 for the target cluster at the next sequencing cycle i+1. To generate the next base call 298, the expectation maximization algorithm observes the means (centroids) and the distributions (covariances) based on the corrected next intensity data 296t to best fit the next available intensity data.

Once the four intensity distributions are determined at the next sequencing cycle i+1 by using the expectation maximization algorithm, the likelihoods of the corrected next intensity data 296t belonging to each of the four intensity distributions are calculated. The greatest likelihood gives the next base call 298.

Note that the base calling pipeline 200 is executed on a cluster-by-cluster basis and is executed in parallel for the multiple clusters in the cluster population. Also, the base calling pipeline 200 is executed repeatedly for successive sequencing cycles of the sequencing run (e.g., for successive 150 sequencing cycles of read 1 and another successive 150 sequencing cycles of read 2 in a paired-end sequencing run).

Least-Squares Solution

Figure 3:
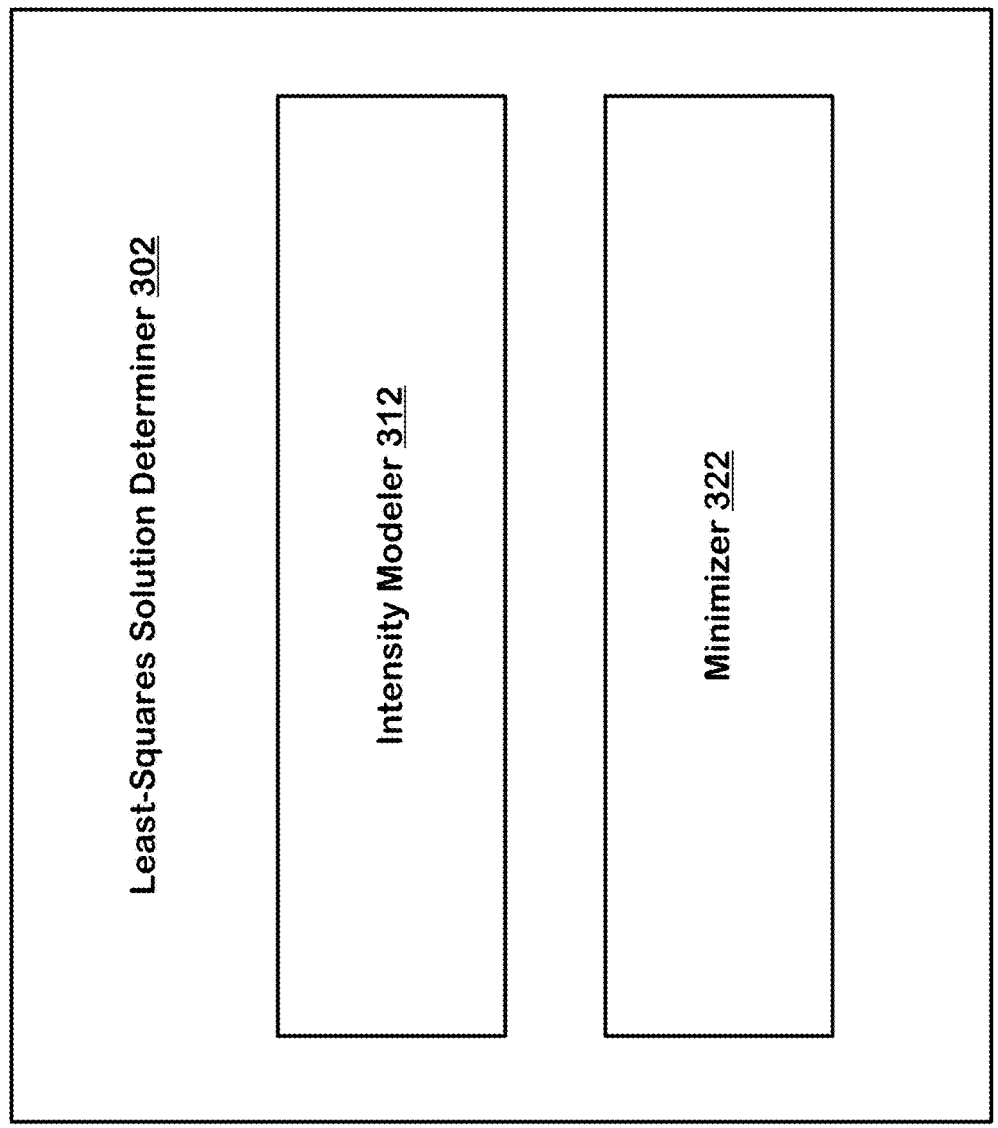
FIG. 3 shows a least-squares solution determiner that implements a least-squares solution disclosed herein.

FIG. 3 shows a least-squares solution determiner that implements a least-squares solution 300 disclosed herein. The least-squares solution 300 determines closed-form expressions for the accumulated intensity correction parameters 262 and the variation correction coefficients 282. The least-squares solution determiner 302 comprises an intensity modeler 312 and a minimizer 322.

The intensity modeler 312 models the relationship between the measured intensity for the target cluster and the variation correction coefficients 282 according to the following expression:

$$y_{C,i} = ax_{C,i} + d_i + n_{C,i} \qquad \text{Equation (1)}$$

where
a is the amplification coefficient for the target cluster
$d_i$ is the channel-specific offset coefficient for intensity channel i
$x_{C,i}$ is the distribution intensity in the intensity channel i for the target cluster at the current sequencing cycle C
$y_{C,i}$ is the measured intensity in the intensity channel i for the target cluster at the current sequencing cycle C
$n_{C,i}$ is the additive noise in the intensity channel i for the target cluster at the current sequencing cycle C The minimizer 322 uses the least-squares solution 300 to minimize the following expression:

$$errorf(\hat{a}, \hat{d}_i) = \sum_{c=1}^{C}\sum_{i=1}^{2}(\hat{a}x_{C,i} + \hat{d}_i - y_{C,i})^2 \qquad \text{Equation (2)}$$

where:
errorf is the error function
$\hat{a}$ is the amplification coefficient for the target cluster
$\hat{d}_i$ is the channel-specific offset coefficient for the intensity channel i
C is the current sequencing cycle Using the chain rule, the minimizer 322 calculates two partial derivatives of the error function with respect to the amplification coefficient $\hat{a}$ and the channel-specific offset coefficients $\hat{d}_i$. The partial derivatives set Equation 2 to zero to minimize the error function:

$$\frac{\partial errorf}{\partial \hat{a}} = \frac{\partial}{\partial \hat{a}}\left[\sum_{c=1}^{C}\sum_{i=1}^{2}(\hat{a}x_{C,i} + \hat{d}_i - y_{C,i})^2\right] = 0 \qquad \text{Equation (3)}$$

$$\frac{\partial errorf}{\partial \hat{d}_i} = \frac{\partial}{\partial \hat{d}_i}\left[\sum_{c=1}^{C}\sum_{i=1}^{2}(\hat{a}x_{C,i} + \hat{d}_i - y_{C,i})^2\right] = 0 \qquad \text{Equation (4)}$$

Channel-specific intensity error $e_{c,i}$ is defined as follows:

$$e_{C,i} = y_{C,i} - x_{C,i} \qquad \text{Equation (5)}$$

Closed-Form Expressions

The first partial derivative determines a closed-form expression for the amplification coefficient $\hat{a}$ as follows:

$$\frac{\partial errorf}{\partial \hat{a}} = \sum_{c=1}^{C}\sum_{i=1}^{2}2x_{C,i}(\hat{a}x_{C,i} + \hat{d}_i - y_{C,i}) = 0 \qquad \text{Equation (6)}$$

$$= \sum_{c=1}^{C}\sum_{i=1}^{2}2x_{C,i}(\hat{a}x_{C,i} - x_{C,i} + \hat{d}_i - y_{C,i} + x_{C,i}) = 0 \qquad \text{Equation (7)}$$

$$= \sum_{c=1}^{C}\sum_{i=1}^{2}x_{C,i}^2(\hat{a}-1) + \hat{d}_i x_{C,i} - e_{C,i}x_{C,i}) = 0 \qquad \text{Equation (8)}$$

$$= (\hat{a}-1)\sum_{c=1}^{C}(x_{C,1}^2 + x_{C,2}^2) + \hat{d}_1\sum_{c=1}^{C}x_{C,1} + \hat{d}_2\sum_{c=1}^{C}x_{C,2} - \qquad \text{Equation (9)}$$

$$\sum_{c=1}^{C}e_{C,1}x_{C,1} - \sum_{c=1}^{C}e_{C,2}x_{C,2} = 0$$

Closed-form expressions $\bar{x}_1$, $\bar{x}_2$, $\bar{e}_1$, $\bar{e}_2$, $\overline{xx}$, and $\overline{xe}$ for the accumulated intensity correction parameters 262 recharacterize Equation 9 as follows:

$$= C(\hat{a}-1)\overline{xx} + C\bar{x}_1\hat{d}_1 + C\bar{x}_2\hat{d}_2 - C\overline{xe} = 0 \quad \text{Equation (10)}$$

$$= (\hat{a}-1)\overline{xx} + \bar{x}_1\hat{d}_1 + \bar{x}_2\hat{d}_2 - \overline{xe} = 0 \quad \text{Equation (11)}$$

where:

$$\bar{x}_1 = \sum_{c=1}^{C} x_{C,1} \quad \text{Intermediate Term (1)}$$

$$\bar{x}_2 = \sum_{c=1}^{C} x_{C,2} \quad \text{Intermediate Term (2)}$$

$$\bar{e}_1 = \sum_{c=1}^{C} e_{c,1} \quad \text{Intermediate Term (3)}$$

$$\bar{e}_2 = \sum_{c=1}^{C} e_{c,2} \quad \text{Intermediate Term (4)}$$

$$\overline{xx} = \sum_{c=1}^{C} \left( x_{C,1}^2 + x_{C,2}^2 \right) \quad \text{Intermediate Term (5)}$$

$$\overline{xe} = \sum_{c=1}^{C} (x_{c,1} e_{c,1} + x_{c,2} e_{c,2}) \quad \text{Intermediate Term (6)}$$

We define each of the accumulated intensity correction parameters 262 as follows:
1) The first accumulated intensity correction parameter $\bar{x}_1$ is the sum of distribution intensities in the first intensity channel measured for the target cluster at each of the preceding sequencing cycles 1 to i−1, and the current sequencing cycle i.
2) The second accumulated intensity correction parameter $\bar{x}_2$ is the sum of distribution intensities in the second intensity channel measured for the target cluster at each of the preceding sequencing cycles 1 to i−1, and the current sequencing cycle i.
3) The third accumulated intensity correction parameter $\bar{e}_1$ is the sum of intensity errors in the first intensity channel calculated for the target cluster at each of the preceding sequencing cycles 1 to i−1, and the current sequencing cycle i.
4) The fourth accumulated intensity correction parameter $\bar{e}_2$ is the sum of intensity errors in the second intensity channel calculated for the target cluster at each of the preceding sequencing cycles 1 to i−1, and the current sequencing cycle i.
5) The fifth accumulated intensity correction parameter $\overline{xx}$ is the sum of distribution centroid-to-origin distances calculated for the target cluster at each of the preceding sequencing cycles 1 to i−1, and the current sequencing cycle i.
6) The sixth accumulated intensity correction parameter $\overline{xe}$ is the sum of distribution intensity-to-intensity error similarity measures calculated for the target cluster at each of the preceding sequencing cycles 1 to i−1, and the current sequencing cycle i.

The second partial derivative determines a closed-form expression for the offset coefficients $\hat{d}_i$ as follows:

$$\frac{\partial errorf}{\partial \hat{d}_i} = \sum_{c=1}^{C} \sum_{i=1}^{2} 2(\hat{a} x_{C,i} + \hat{d}_i - y_{C,i}) = 0 \quad \text{Equation (12)}$$

$$= \sum_{c=1}^{C} \sum_{i=1}^{2} (\hat{a} x_{C,i} - x_{C,i} + \hat{d}_i - y_{C,i} + x_{C,i}) = 0 \quad \text{Equation (13)}$$

$$= \sum_{c=1}^{C} \sum_{i=1}^{2} x_{C,i}^2 \left( (\hat{a}-1) + \sum_{i=1}^{2} \hat{d}_i + \sum_{c=1}^{C} x_{C,i} \right) = 0 \quad \text{Equation (14)}$$

Then, for each intensity channel:

$$= C(\hat{a}-1)\bar{x}_i + C\hat{d}_i - C\bar{e}_i = 0 \quad \text{Equation (15)}$$

$$= (\hat{a}-1)\bar{x}_i + \hat{d}_i - \bar{e}_i = 0 \quad \text{Equation (16)}$$

For the first intensity channel, i.e., i=1:

$$\hat{d}_1 = \bar{e}_1 + (1-\hat{a})\bar{x}_1 \quad \text{Equation (17)}$$

where:
$\hat{d}_1$ is the offset coefficient for the first intensity channel
For the second intensity channel, i.e., i=2:

$$\hat{d}_2 = \bar{e}_2 + (1-\hat{a})\bar{x}_2 \quad \text{Equation (18)}$$

where:
$\hat{d}_2$ is the offset coefficient for the second intensity channel
Substituting Equations 17 and 18 in Equation 11:

$$\frac{\partial errorf}{\partial \hat{a}} = \quad \text{Equation (19)}$$
$$(\hat{a}-1)\overline{xx} + \bar{x}_1[\bar{e}_1 + (1-\hat{a})\bar{x}_1] + \bar{x}_2[\bar{e}_2 + (1-\hat{a})\bar{x}_2] - \overline{xe} = 0$$

$$= (\hat{a}-1)\overline{xx} + (1-\hat{a})\bar{x}_1^2 + (1-\hat{a})\bar{x}_2^2 + \bar{x}_1\bar{e}_1 + \bar{x}_2\bar{e}_2 - \overline{xe} = 0 \quad \text{Equation (20)}$$

$$= (\hat{a}-1)(\overline{xx} - \bar{x}_1^2 - \bar{x}_2^2) + \bar{x}_1\bar{e}_1 + \bar{x}_2\bar{e}_2 - \overline{xe} = 0 \quad \text{Equation (21)}$$

$$\hat{a} - 1 = \frac{\bar{x}_1\bar{e}_1 + \bar{x}_2\bar{e}_2 - \overline{xe}}{\overline{xx} - \bar{x}_1^2 - \bar{x}_2^2} \quad \text{Equation (22)}$$

$$\hat{a} = 1 + \frac{\bar{x}_1\bar{e}_1 + \bar{x}_2\bar{e}_2 - \overline{xe}}{\overline{xx} - \bar{x}_1^2 - \bar{x}_2^2} \quad \text{Equation (23)}$$

where:
$\hat{a}$ is the amplification coefficient for the target cluster

In another implementation, to reduce the memory requirements per cluster, the common offset coefficient for the different intensity channels (e.g., the first and the second intensity channels) is determined as follows by introducing the constraint $\hat{d}_1 = \hat{d}_2$:

$$\bar{x} = \frac{1}{2C} \sum_{c=1}^{C} (x_{C,1} + x_{C,2}) \quad \text{Intermediate Term (1.1)}$$

$$\overline{xx} = \frac{1}{C} \sum_{c=1}^{C} \left( x_{C,1}^2 + x_{C,2}^2 \right) \quad \text{Intermediate Term (2.1)}$$

-continued $$\bar{e} = \frac{1}{2C}\sum_{c=1}^{C}(e_{C,1} + e_{C,2})$$ Intermediate Term (3.1)

$$\overline{xe} = \frac{1}{C}\sum_{c=1}^{C}(x_{C,1}e_{C,1} + x_{C,2}e_{C,2})$$ Intermediate Term (4.1)

$$\hat{a} = 1 + \frac{\overline{xe} - 2\bar{x}\bar{e}}{\overline{xx} - 2\bar{x}^2}$$ Equation (24)

$$\hat{d}_1 = \bar{e} + \bar{x}(1 - \hat{a})$$ Equation (25)

$$\hat{d}_2 = \bar{e} + \bar{x}(1 - \hat{a})$$ Equation (26)

It would be apparent to one skilled in the art that the least-squares solution 300 is executed in advance of the sequencing run to determine the closed-form expressions. Once determined, the closed-form expressions are applied to the intensity values generated during the sequencing run on a cluster-by-cluster and iteratively at each sequencing cycle of the sequencing run.

Intensity Correction Parameters

The following discussion focuses on how the six intensity correction parameters, namely, the distribution intensity in the first intensity channel, the distribution intensity in the second intensity channel, the intensity error in the first intensity channel, the intensity error in the second intensity channel, the distribution centroid-to-origin distance, and the distribution intensity-to-intensity error similarity measure are determined for the target cluster at the current sequencing cycle.

It would be apparent to one skilled in the art that the number of the intensity correction parameters would change depending upon the number of intensity channels. For example, in the case of the four-channel implementation, four channel-specific distribution intensities and four channel-specific intensity errors would be calculated for the four intensity channels, respectively.

Figure 4:
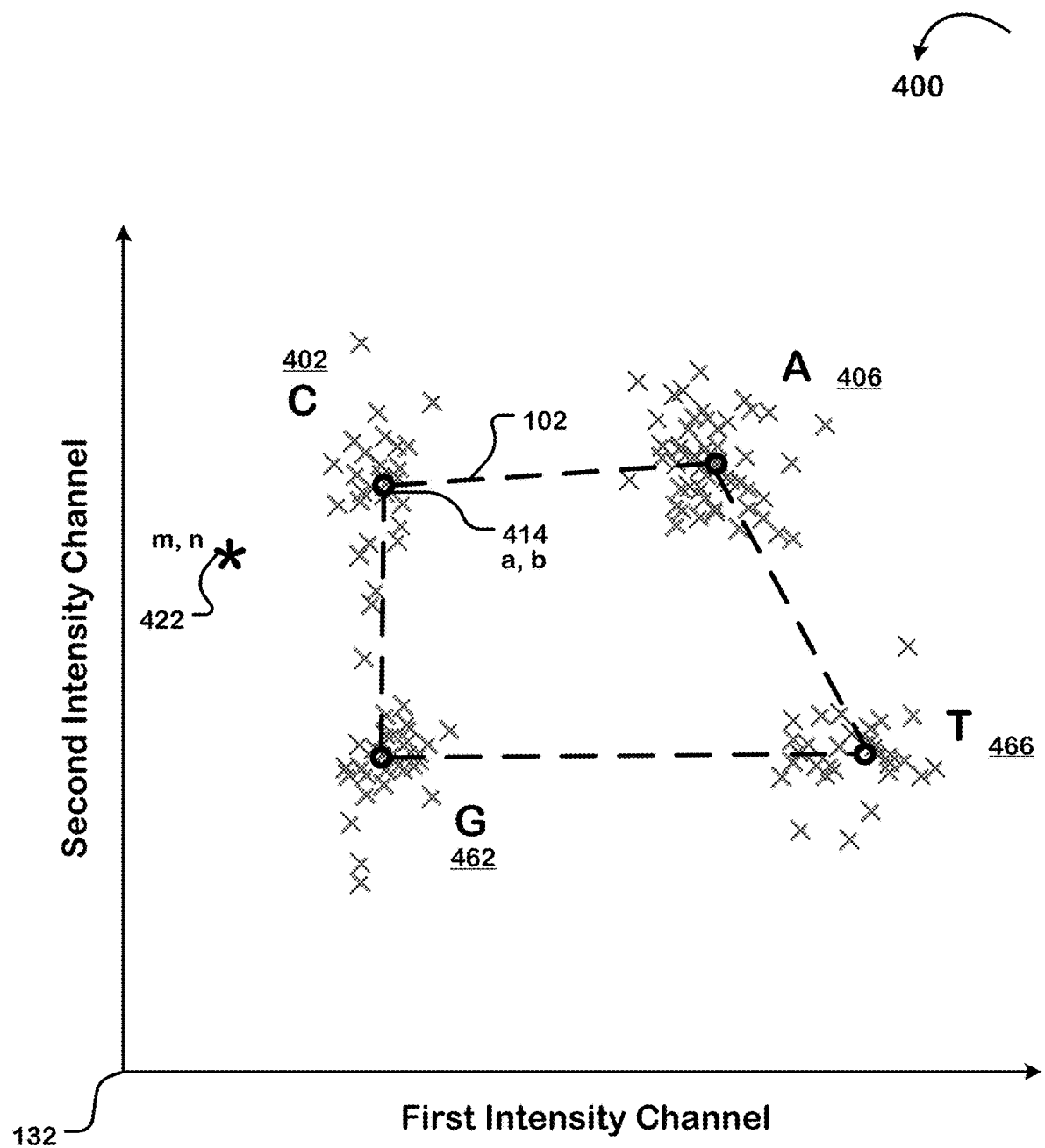
FIG. 4 shows an example of how the channel-specific distribution intensities are measured for a target cluster at a current sequencing cycle.

FIG. 4 shows an example 400 of how the channel-specific distribution intensities are measured for the target cluster at the current sequencing cycle i. In FIG. 4, the "✗" symbol represents the intensity values in the first and the second intensity channels registered for cluster 1 at the current sequencing cycle i and the preceding sequencing cycles 1 to i−1.

In FIG. 4, the four intensity distributions C 402, A 406, G 462, and T 466 are connected to form the constellation 102 for cluster 1. In FIG. 4, the "*" symbol represents the measured intensities "m, n" 422 in the first and the second intensity channels registered for the cluster 1 at the current sequencing cycle i. Since the measured intensities "m, n" 422 are closest to centroid 414 of the intensity distribution C 402, cluster 1 belongs to the intensity distribution C 402, and therefore assigned the base call C at the current sequencing cycle i.

Furthermore, since cluster 1 belongs to the C intensity distribution 402, intensity values "a, b" at the centroid 414 are the distribution intensities for cluster 1 at the current sequencing cycle i. Also, "a" is the channel-specific distribution intensity for the first intensity channel, and "b" is the channel-specific distribution intensity for the second intensity channel.

Figure 5:
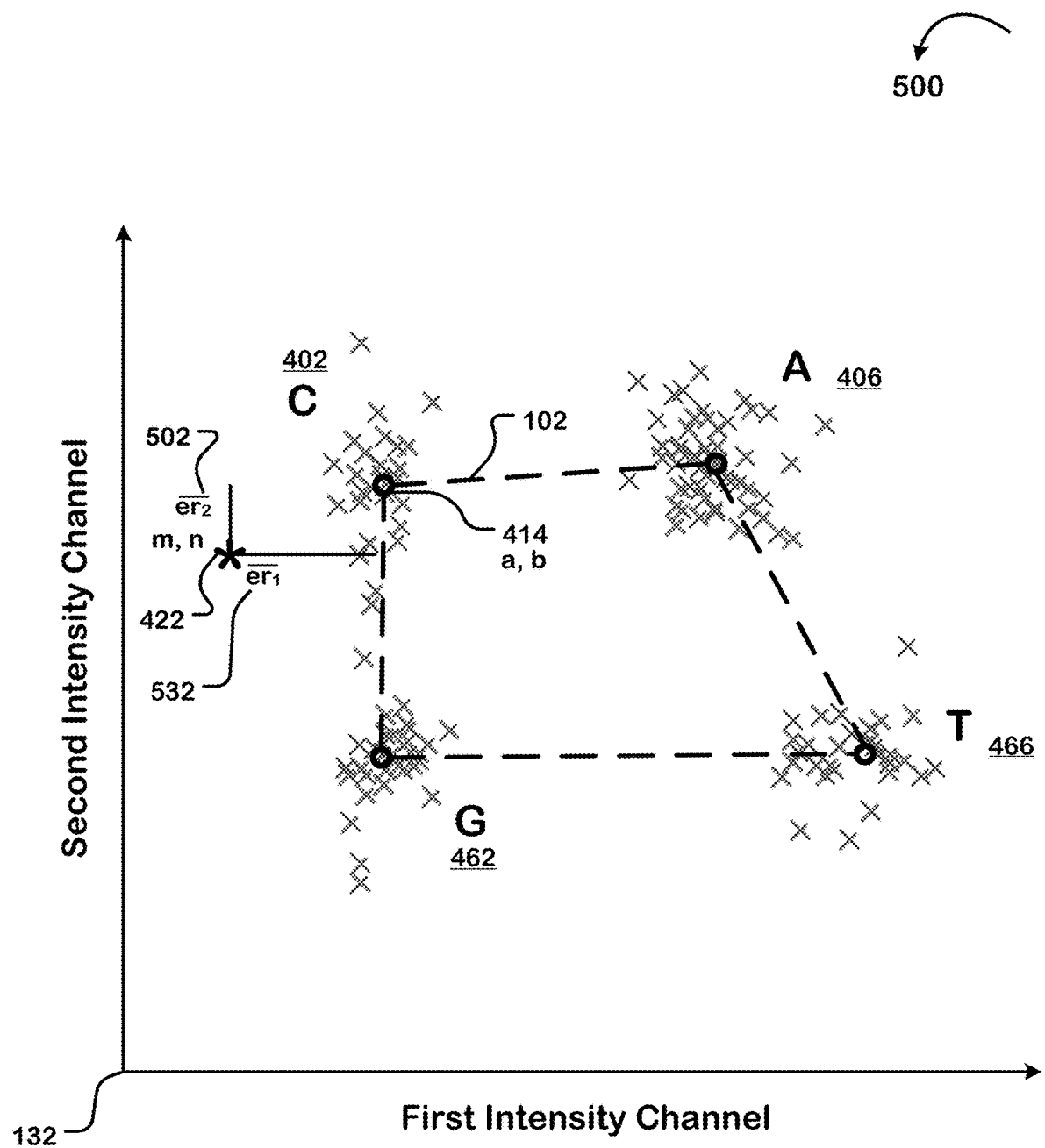
FIG. 5 shows an example of how the channel-specific intensity errors are calculated for the target cluster at the current sequencing cycle.

FIG. 5 shows an example 500 of how the channel-specific intensity errors are calculated for the target cluster at the current sequencing cycle i. The intensity error ($\overline{er}_1$) 532 in the first intensity channel is calculated for cluster 1 at the current sequencing cycle i as a difference between the channel-specific measured intensity in the first intensity channel (m) and the channel-specific distribution intensity in the first intensity channel (a):

$$\overline{er}_1 = m - a$$ Equation (27)

The intensity error ($\overline{er}_2$) 502 in the second intensity channel is calculated for cluster 1 at the current sequencing cycle i as a difference between the channel-specific measured intensity in the second intensity channel (n) and the channel-specific distribution intensity in the second intensity channel (b):

$$\overline{er}_2 = n - b$$ Equation (28)

Figure 6:
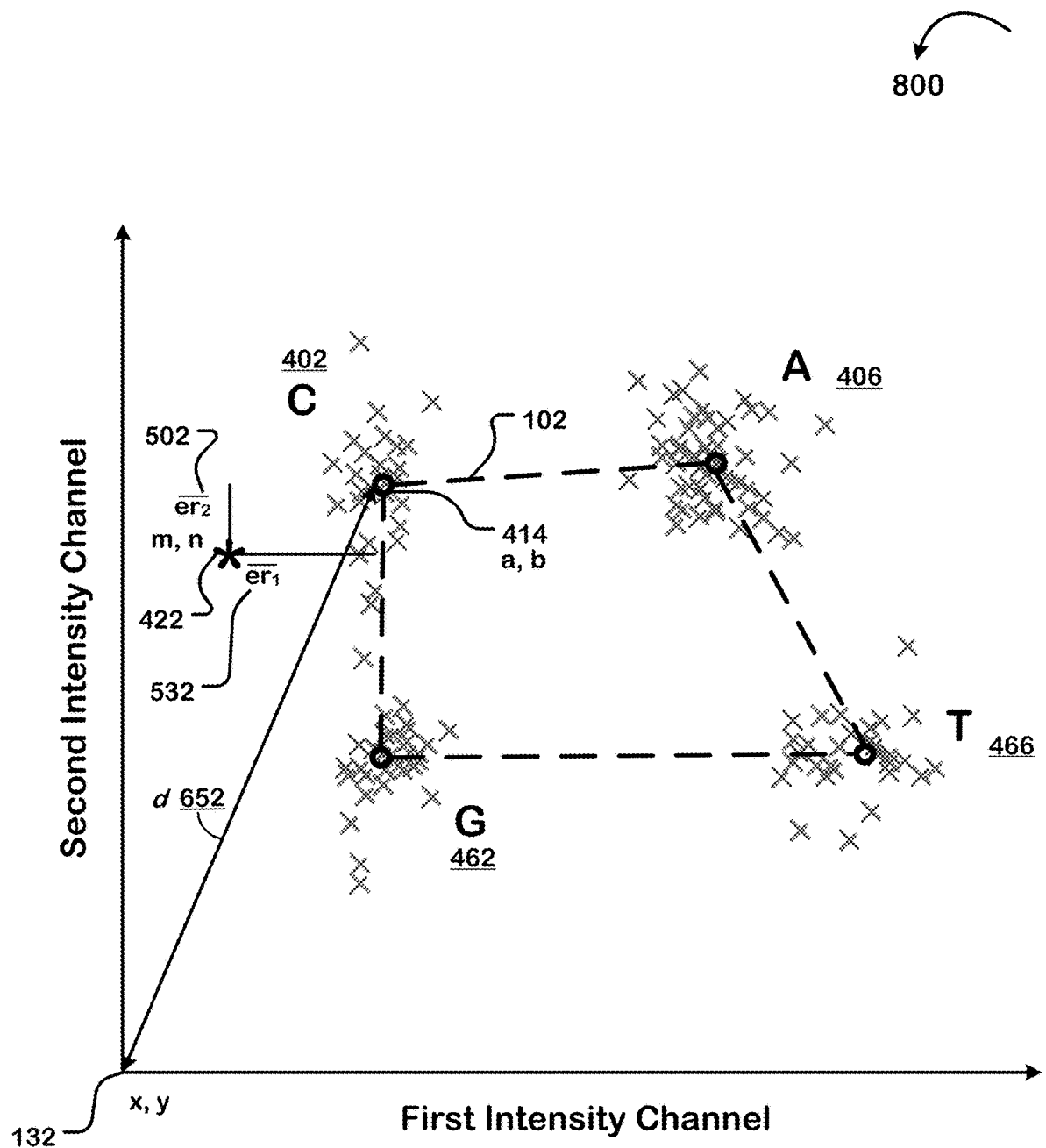
FIG. 6 shows an example of how the distribution centroid-to-origin distances are calculated for the target cluster at the current sequencing cycle.

FIG. 6 shows an example 600 of how the distribution centroid-to-origin distances are calculated for the target cluster at the current sequencing cycle i. Cluster 1 belongs to the C intensity distribution 402, and the intensity values "a, b" at the centroid 414 are the distribution intensities for cluster 1 at the current sequencing cycle i.

The distribution centroid-to-origin distance is calculated for cluster 1 at the current sequencing cycle i as the Euclidean distance (d) 652 between the centroid 414 and the origin 132 "x, Y":

$$d = \sqrt{(a-x)^2 + (b-y)^2}$$ Equation (29)

The distribution intensity-to-intensity error similarity measure is calculated for cluster 1 at the current sequencing cycle i as a summation of channel-wise dot products between the channel-specific distribution intensities and the channel-specific intensity errors:

$$\text{similarity measure} = \overline{er}_1 \cdot a + \overline{er}_2 \cdot b$$ Equation (30)

where:
● is the dot product operator

Base Calling Pipeline

FIG. 7 depicts another example of a base calling pipeline 700 that implements the variation correction logic. Consider that the current sequencing cycle i is the twenty-fifth sequencing cycle of the sequencing run, i.e., i=25. The preceding sequencing cycle i−1 is the twenty-fourth sequencing cycle of the sequencing run, i.e., i−1=24. The next sequencing cycle i+1 is the twenty-sixth sequencing cycle of the sequencing run, i.e., i+1=26. The subsequent sequencing cycle i+2 is the twenty-seventh sequencing cycle of the sequencing run, i.e., i+2=27.

Preceding Sequencing Cycles

At each of the first to the twenty-fourth sequencing cycles, respective sets of accumulated intensity correction parameters are determined from respective sets of intensity correction parameters. Preceding accumulated intensity correction parameters 702 for the target cluster are intensity correction parameter-wise accumulations of the twenty four sets of the intensity correction parameters. In the two-channel implementation, each of the twenty four sets of the intensity correction parameters includes the six intensity correction parameters, namely, the distribution intensity in the first intensity channel, the distribution intensity in the second intensity channel, the intensity error in the first intensity channel, the intensity error in the second intensity channel, the distribution centroid-to-origin distance, and the distribution intensity-to-intensity error similarity. Each of the twenty four sets of the accumulated intensity correction parameters includes the six accumulated intensity correction parameters $\bar{x}_1$, $\bar{x}_2$, $\bar{e}_1$, $\bar{e}_2$, $\overline{xx}$, and $\overline{xe}$.

The preceding accumulated intensity correction parameters 702 are metadata (or statistics) about the underlying preceding intensity values and preceding intensity correction parameters from which they are calculated. As a result, compared to the underlying preceding intensity values and the preceding intensity correction parameters, the preceding accumulated intensity correction parameters 702 have a much smaller memory footprint. The preceding accumulated intensity correction parameters 702 are cached in memory during the sequencing run and are accumulated with current intensity correction parameters 732 for the target cluster to generate current accumulated intensity correction parameters 742 for the target cluster, as depicted by triangle 734.

In one implementation, the preceding accumulated intensity correction parameters 702 are stored in a quantized fixed bit width format. For example, one or two bytes can be used to store each preceding accumulated intensity correction parameter in the preceding accumulated intensity correction parameters 702.

Current Sequencing Cycle

Current measured intensity 712 for the target cluster includes the intensity values registered for the target cluster at the twenty-fifth sequencing cycle. Based on the current measured intensity 712, a current base call 722 is called for the target cluster at the twenty-fifth sequencing cycle (e.g., by using the expectation maximization algorithm).

Next Sequencing Cycle

Based on the current base call 722, the current intensity correction parameters 732 are determined for the target cluster. The current accumulated intensity correction parameters 742 are calculated for the target cluster based on accumulating the preceding accumulated intensity correction parameters 702 with the current intensity correction parameters 732, as depicted by the triangle 734. One example of the accumulation is summing. In the summing implementation, the current accumulated intensity correction parameters 742 are calculated by summing the preceding accumulated intensity correction parameters 702 and the current intensity correction parameters 732 on an intensity correction parameter-basis (as shown above in Intermediate Terms 1 to 6).

Another example of the accumulation is averaging:

$$\bar{x}_1 = \frac{1}{C}\sum_{c=1}^{C} x_{C,1}$$ Intermediate Term (1.2)

$$\bar{x}_2 = \frac{1}{C}\sum_{c=1}^{C} x_{C,2}$$ Intermediate Term (2.2)

$$\bar{e}_1 = \frac{1}{C}\sum_{c=1}^{C} e_{C,1}$$ Intermediate Term (3.2)

$$\bar{e}_2 = \frac{1}{C}\sum_{c=1}^{C} e_{C,2}$$ Intermediate Term (4.2)

-continued $$\overline{xx} = \frac{1}{C}\sum_{c=1}^{C}\left(x_{C,1}^2 + x_{C,2}^2\right)$$ Intermediate Term (5.2)

$$\overline{xe} = \frac{1}{C}\sum_{c=1}^{C}(x_{C,1}e_{C,1} + x_{C,2}e_{C,2})$$ Intermediate Term (6.2)

where C is the index for the current sequencing cycle i, i.e., C=25 in the example discussed herein Based on the Intermediate Terms 1.2 to 6.2, we define each of the accumulated intensity correction parameters as follows:

1) The first accumulated intensity correction parameter $\bar{x}_1$ is the average of the distribution intensities in the first intensity channel measured for the target cluster at each of the preceding sequencing cycles 1 to i−1, and the current sequencing cycle i.
2) The second accumulated intensity correction parameter $\bar{x}_2$ is the average of the distribution intensities in the second intensity channel measured for the target cluster at each of the preceding sequencing cycles 1 to i−1, and the current sequencing cycle i.
3) The third accumulated intensity correction parameter $\bar{e}_1$ is the average of the intensity errors in the first intensity channel calculated for the target cluster at each of the preceding sequencing cycles 1 to i−1, and the current sequencing cycle i.
4) The fourth accumulated intensity correction parameter $\bar{e}_2$ is the average of the intensity errors in the second intensity channel calculated for the target cluster at each of the preceding sequencing cycles 1 to i−1, and the current sequencing cycle i.
5) The fifth accumulated intensity correction parameter $\overline{xx}$ is the average of the distribution centroid-to-origin distances calculated for the target cluster at each of the preceding sequencing cycles 1 to i−1, and the current sequencing cycle i.
6) The sixth accumulated intensity correction parameter $\overline{xe}$ is the average of the distribution intensity-to-intensity error similarity measures calculated for the target cluster at each of the preceding sequencing cycles 1 to i−1, and the current sequencing cycle i.

Compact Representation

In one implementation, the preceding accumulated intensity correction parameters 702 are stored in a compact representation (e.g., a summed representation or an averaged representation). In the averaging implementation, the preceding accumulated intensity correction parameters 702 are stored in their averaged representation and first multiplied by the number of sequencing cycles over which they are accumulated to retrieve the pre-average representation, i.e., 24 is the multiplier in the example discussed herein.

Then, the result of the multiplication, i.e., the pre-average representation is summed with the current intensity correction parameters 732 on the intensity correction parameter-basis. Then, the result of the sum is divided by the index C for the current sequencing cycle i (C=25) to determine the current accumulated intensity correction parameters 742.

Consider that $\bar{x}_1^{24}$ is the first accumulated intensity correction parameter for the twenty-fourth sequencing cycle. Consider that $x^{25}_{C,1}$ is the distribution intensity in the first intensity channel for the twenty-fifth sequencing cycle. Consider that $\bar{x}_1^{25}$ is the first accumulated intensity correction parameter for the twenty-fifth sequencing cycle and used to correct the measured intensity for the twenty-sixth sequencing cycle. Then, $$\overline{x}_1^{25} = \frac{\left[\left(\overline{x}_1^{24} * 24\right) + x_{C,1}^{25}\right]}{25}$$

Consider that $\overline{x}_2^{24}$ is the second accumulated intensity correction parameter for the twenty-fourth sequencing cycle. Consider that $x^{25}{}_{C,2}$ is the distribution intensity in the second intensity channel for the twenty-fifth sequencing cycle. Consider that $\overline{x}_2^{25}$ is the second accumulated intensity correction parameter for the twenty-fifth sequencing cycle and used to correct the measured intensity for the twenty-sixth sequencing cycle. Then, $$\overline{x}_2^{25} = \frac{\left[\left(\overline{x}_2^{24} * 24\right) + x_{C,2}^{25}\right]}{25}$$

Consider that $\overline{e}_1^{24}$ is the third accumulated intensity correction parameter for the twenty-fourth sequencing cycle. Consider that $e^{25}{}_{C,1}$ is the intensity error in the first intensity channel for the twenty-fifth sequencing cycle. Consider that $\overline{e}_1^{25}$ is the third accumulated intensity correction parameter for the twenty-fifth sequencing cycle and used to correct the measured intensity for the twenty-sixth sequencing cycle. Then, $$\overline{e}_1^{25} = \frac{\left[\left(\overline{e}_1^{24} * 24\right) + e_{C,1}^{25}\right]}{25}$$

Consider that $\overline{e}_2^{24}$ is the fourth accumulated intensity correction parameter for the twenty-fourth sequencing cycle. Consider that $e^{25}{}_{C,2}$ is the intensity error in the second intensity channel for the twenty-fifth sequencing cycle. Consider that $\overline{e}_1^{25}$ is the fourth accumulated intensity correction parameter for the twenty-fifth sequencing cycle and used to correct the measured intensity for the twenty-sixth sequencing cycle. Then, $$\overline{e}_2^{25} = \frac{\left[\left(\overline{e}_2^{24} * 24\right) + e_{C,2}^{25}\right]}{25}$$

Consider that $\overline{xx}^{24}$ is the fifth accumulated intensity correction parameter for the twenty-fourth sequencing cycle. Consider that $[(x_{C,1}^{25})^2+(x_{C,2}^{25})^2]$ is the distribution centroid-to-origin distance for the twenty-fifth sequencing cycle. Consider that $\overline{xx}^{25}$ is the fifth accumulated intensity correction parameter for the twenty-fifth sequencing cycle and used to correct the measured intensity for the twenty-sixth sequencing cycle. Then, $$\overline{xx}^{25} = \frac{\left[\left(\overline{xx}^{24} * 24\right) + \left[(x_{C,1}^{25})^2 + (x_{C,2}^{25})^2\right]\right]}{25}$$

Consider that $\overline{xe}^{24}$ is the sixth accumulated intensity correction parameter for the twenty-fourth sequencing cycle. Consider that $[(x_{C,1}^{25}e_{C,1}^{25})+(x_{C,2}^{25}e_{C,2}^{25})]$ is the distribution intensity-to-intensity error similarity measure for the twenty-fifth sequencing cycle. Consider that $\overline{xe}^{25}$ is the sixth accumulated intensity correction parameter for the twenty-fifth sequencing cycle and used to correct the measured intensity for the twenty-sixth sequencing cycle. Then, $$\overline{xe}^{25} = \frac{\left[\left(\overline{xe}^{24} * 24\right) + \left[(x_{C,1}^{25}e_{C,1}^{25}) + (x_{C,2}^{25}e_{C,2}^{25})\right]\right]}{25}$$

The current accumulated intensity correction parameters 742 are metadata (or statistics) about the current measured intensity 712 and the current intensity correction parameters 732. As a result, compared to the current measured intensity 712 and the current intensity correction parameters 732, the current accumulated intensity correction parameters 742 have a much smaller memory footprint. The current accumulated intensity correction parameters 742 are cached in memory during the sequencing run and are accumulated with next intensity correction parameters 794 for the target cluster to generate next accumulated intensity correction parameters 796 for the target cluster, as depicted by triangle 784.

In one implementation, the current accumulated intensity correction parameters 742 are stored in a quantized fixed bit width format. For example, one or two bytes can be used to store each preceding accumulated intensity correction parameter in the current accumulated intensity correction parameters 742.

The current accumulated intensity correction parameters 742 are used to determine a current amplification coefficient 752 for the target cluster. This includes executing the closed-form expression in Equation 23 in dependence upon the current accumulated intensity correction parameters 742.

The current accumulated intensity correction parameters 742 and the current amplification coefficient 752 are used to determine current channel-specific offset coefficients 762 for the target cluster. This includes executing the closed-form expressions in Equations 17 and 18 in dependence upon the current accumulated intensity correction parameters 742 and the amplification coefficient 752.

The current amplification coefficient 752 and the current channel-specific offset coefficients 762 are used to correct a next measured intensity 772 measured for the target cluster at the twenty-sixth sequencing cycle. In one implementation, the correcting includes channel-wise subtracting the current channel-specific offset coefficients 762 from the next measured intensity 772 to generate next shifted intensity, and dividing the next shifted intensity by the current amplification coefficient 752 to generate next corrected measured intensity 782 for the target cluster.

Then, a next base call 792 is called for the target cluster at the twenty-sixth sequencing cycle using the next corrected measured intensity 782. This is accomplished by providing the next corrected measured intensity 782 as input to the base caller 212 (e.g., by using the expectation maximization algorithm).

Subsequent Sequencing Cycle

A controller (not shown) iterates the base calling pipeline 700 for successive sequencing cycles of the sequencing run, as exemplified by operations 794, 796, 798, and 799. For example, for the twenty-seventh sequencing cycle, the current accumulated intensity correction parameters 742 serve as the preceding accumulated intensity correction parameters 702, as depicted by triangle 784. Note that the base calling pipeline 700 is executed on a cluster-by-cluster basis and is executed in parallel for the multiple clusters in the cluster population.

Weighted Least-Squares Solution

Figure 8:
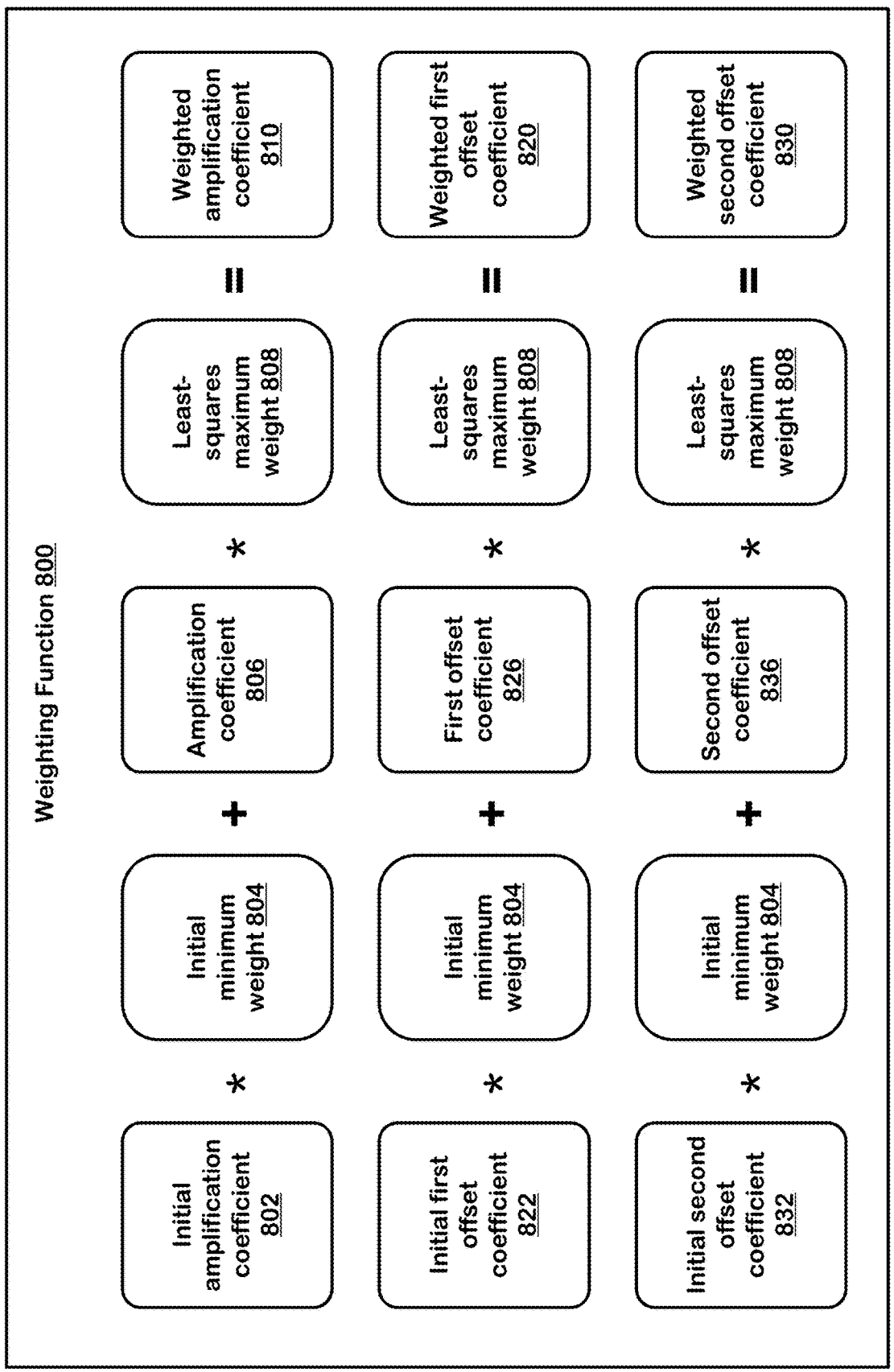
FIG. 8 shows one implementation of a weighting function described herein.

FIG. 8 shows one implementation of a weighting function 800 described herein. Since the least-squares solution 300 can take several sequencing cycles to converge, the weighting function 800 is used to attenuate the variation correction coefficients in initial sequencing cycles of the sequencing run, and to amplify the variation correction coefficients in later sequencing cycles of the sequencing run.

The weighting function 800 works as follows. First, an initial amplification coefficient 802 and initial offset coefficients 822 and 832 are initialized. In one implementation, the initial amplification coefficient 802 is initialized at a first sequencing cycle of the sequencing run with a predetermined value (e.g., "1") and the initial offset coefficients 822 and 832 are initialized at the first sequencing cycle with a predetermined value (e.g., "0"). The weighting function 800 combines (e.g., sums) the initial amplification coefficient 802 with the amplification coefficients 806 (determined by the least-squares solution 300), and combines the initial first and second offset coefficients 822 and 832 with the first and second offset coefficients 826 and 836 (determined by the least-squares solution 300), such that the amplification coefficient 806 and the first and second offset coefficients 826 and 836 are attenuated in the initial sequencing cycles and amplified in the later sequencing cycles.

In one implementation, the weighting function 800 applies (e.g., multiplies) an initial minimum weight (inimin weight) 804 to the initial amplification coefficient 802 and the initial first and second offset coefficients 822 and 832, and a least-squares maximum weight (lsqmax weight) 808 to the amplification coefficient 806 and the first and second offset coefficients 826 and 836, such that:

$$lsq \text{ max weight} = \left(0, \frac{c-p}{c}\right) \quad \text{Equation (31)}$$

$$ini \text{ min weight} = \left(1, 1 - \left[\frac{c-p}{c}\right]\right) \quad \text{Equation (32)}$$

where:
c is an index of the current sequencing cycle
p is a number between 2 to 7
For the first sequencing cycle, i.e., c=1, and for p=2, the expression $$\left(\frac{c-p}{c}\right)$$

equals to "−1." Then, between "0" and "−1," the lsqmax weight 808 selects the maximum of the two values, i.e., 0. The expression $$\left(1 - \left[\frac{c-p}{c}\right]\right)$$

equals to "2." Then, between "1" and "2," the inimin weight 804 selects the minimum of the two values, i.e., 1.

Continuing ahead, 0 from the lsqmax weight 808 is be multiplied with the amplification coefficient 806 and the first and second offset coefficients 826 and 836, and 1 from the inimin weight 804 is multiplied with the initial amplification coefficient 802 and the initial first and second offset coefficients 822 and 832. The results of the two multiplications are summed to generate the weighted amplification coefficient 810 and the weighted first and second offset coefficients 820 and 830.

As the sequencing run progresses and the value of the index "c" increments, and the values of the lsqmax weight 808 and the inimin weight 804 also change and applied analogously, such that the amplification coefficient 806 and the first and second offset coefficients 826 and 836 (learned from the least-squares solution 300) are progressively amplified at each successive sequencing cycle.

The weighting function 800 generates the weighted amplification coefficient 810 and the weighted first and second offset coefficients 820 and 830, which are used to correct the measured intensities for the target cluster at the next sequencing cycles i+1 and to generate the corrected measured intensities for base calling the target cluster at the next sequencing cycles i+1:

$$\hat{a} = 1 + \frac{W\overline{xe} - \overline{x}_1\overline{e}_1 - \overline{x}_2\overline{e}_2}{W\overline{xx} - \overline{x}_1^2 - \overline{x}_2^2} \quad \text{Equation (33)}$$

$$\hat{d}_1 = \frac{-\overline{x}_1 W\overline{xe} + (W\overline{xx} - \overline{x}_2^2)\overline{e}_1 + \overline{x}_1\overline{x}_2\overline{e}_2}{W(W\overline{xx} - \overline{x}_1^2 - \overline{x}_2^2)} \quad \text{Equation (34)}$$

$$\hat{d}_2 = \frac{-\overline{x}_2 W\overline{xe} + (W\overline{xx} - \overline{x}_1^2)\overline{e}_2 + \overline{x}_1\overline{x}_2\overline{e}_1}{W(W\overline{xx} - \overline{x}_1^2 - \overline{x}_2^2)} \quad \text{Equation (35)}$$

where:
W is the weight

Maximum Likelihood Solution

FIG. 9 shows one implementation of directly applying maximum likelihood weights 906, 908, and 910 to the variation correction coefficients. The maximum likelihood weights 906, 908, and 910 are generated by applying a maximum likelihood solution 900 to probability distributions 902 of historical values observed for the variation correction coefficients in previous sequencing runs. FIG. 9 also illustrates accumulated intensity correction parameters 904.

The maximum likelihood weights 906, 908, and 910 are a function of the current sequencing cycle, as represented by the index "C." The maximum likelihood weights 906, 908, and 910 change on a sequencing cycle-basis in dependence upon the index C. The maximum likelihood weights 906, 908, and 910 are also a function of the additive noise, as represented by the character "n." The sigma term "σ" represents the range of variation in the historical values observed for the respective variation correction coefficient, i.e., variance ($\sigma^2$). In some implementations, the sigma term for the additive noise can be estimated using the maximum likelihood solution 900 or can be user-specified. The sigma terms for the amplification coefficient, the channel-specific offset coefficients, and the additive noise are determined on a sequencing run-basis and kept fixed for all the sequencing cycles of the sequencing run. The sigma terms incorporate apriori knowledge about the uncertainty observed in the variation correction coefficients.

Some example values of the sigma terms are:
'ml_chanest_sigma_a', 0.15
'ml_chanest_sigma_d1', 0.1
'ml_chanest_sigma_d2', 0.02
'ml_chanest_sigma_n', 0.14

In one implementation, a center/initial/mean value for the probability distribution of the amplification coefficient is set to be "1," and a center/initial/mean value for the probability distributions of the channel-specific offset coefficients is set to be "0."

Smaller values of the sigma terms for the amplification coefficient and the channel-specific offset coefficients in the maximum likelihood weights 906, 908, and 910 indicate low variation in their respective historical values. This results in higher values of the maximum likelihood weights 906, 908, and 910. This in turn leads to a weighted amplification coefficient 920 that is weighted in favor of the center value 1, and weighted channel-specific offset coefficients 930 and 940 that are weighted in favor of the center value 0, particularly in the early sequencing cycles.

Conversely, larger values of the sigma terms for the amplification coefficient and the channel-specific offset coefficients in the maximum likelihood weights 906, 908, and 910 indicate high variation in their respective historical values. This results in lower values of the maximum likelihood weights 906, 908, and 910. This in turn leads to the weighted amplification coefficient 920 that is weighted in favor of the output of the least-squares solution 300 (e.g., Equation 23), and the weighted channel-specific offset coefficients 930 and 940 that are weighted in favor of the output of the least-squares solution 300 (e.g., Equations 17 and 18), particularly in the later sequencing cycles.

The maximum likelihood weights 906, 908, and 910 are directly incorporated to calculate the weighted amplification coefficient 920 and the weighted channel-specific offset coefficients 930 and 940, respectively.

Exponential Decay Factor Solution

FIG. 10 shows one implementation of applying an exponential decay factor to the variation correction coefficients. Exponential decay logic 1000 is based on so-called "tau" and "stats.cycle." The term "stats.cycle" refers to the current sequencing cycle.

Tau is set to a predetermined value depending on the degree of time variance observed in the intensity correction parameters. If the intensity correction parameters are time-invariant, then tau can be set to infinity. If the intensity correction parameters are rapidly time-variant, then tau can be set to a small value. In one implementation, tau is set to thirty-two.

Consider that tau is thirty-two. Then, according to statements 1002, 1004, and 1006, the decay factor is "1" for sequencing cycles one to thirty-one, and this results in no decay in the accumulated intensity correction parameters. For sequencing cycles thirty-two and above, the decay factor is thirty-one over thirty-two, based on statement 1008. The exponential decay character comes from the fact that, in statements 1010, 1012, 1014, 1016, 1018, and 1020, each of the accumulated intensity correction parameters is multiplied by the decay factor at each successive sequencing cycle, as shown below:

For sequencing cycle 32, $$\text{decay factor} = \frac{31}{32}$$

$$\bar{x}_1^D = \frac{31}{32} * \bar{x}_1 \quad \text{Decayed Intermediate Term (1.3)}$$

$$\bar{x}_2^D = \frac{31}{32} * \bar{x}_2 \quad \text{Decayed Intermediate Term (2.3)}$$

$$\bar{e}_1^D = \frac{31}{32} * \bar{e}_1 \quad \text{Decayed Intermediate Term (3.3)}$$

$$\bar{e}_2^D = \frac{31}{32} * \bar{e}_2 \quad \text{Decayed Intermediate Term (4.3)}$$

$$\overline{xx}^D \frac{31}{32} * \overline{xx} \quad \text{Decayed Intermediate Term (5.3)}$$

$$\overline{xe}^D \frac{31}{32} * \overline{xe} \quad \text{Decayed Intermediate Term (6.3)}$$

For sequencing cycle 33, $$\text{decay factor} = \left[\frac{31}{32}\right]^2$$

$$\bar{x}_1^D = \left[\frac{31}{32}\right]^2 * \bar{x}_1 \quad \text{Decayed Intermediate Term (1.4)}$$

$$\bar{x}_2^D = \left[\frac{31}{32}\right]^2 * \bar{x}_2 \quad \text{Decayed Intermediate Term (2.4)}$$

$$\bar{e}_1^D = \left[\frac{31}{32}\right]^2 * \bar{e}_1 \quad \text{Decayed Intermediate Term (3.4)}$$

$$\bar{e}_2^D = \left[\frac{31}{32}\right]^2 * \bar{e}_2 \quad \text{Decayed Intermediate Term (4.4)}$$

$$\overline{xx}^D \left[\frac{31}{32}\right]^2 * \overline{xx} \quad \text{Decayed Intermediate Term (5.4)}$$

$$\overline{xe}^D \left[\frac{31}{32}\right]^2 * \overline{xe} \quad \text{Decayed Intermediate Term (6.4)}$$

In FIG. 10, the accumulated intensity correction parameters are accumulated using the sum operation. In the averaging implementation of the exponential decay factor, the accumulated intensity correction parameters are accumulated using the average operation. In the averaging implementation of the exponential decay factor, the divisor "C" in the Intermediate Terms 1.2 to 6.2 is kept fixed after the tau number of sequencing cycles of the sequencing run, i.e., after thirty-second sequencing cycle of the sequencing run.

In some implementations, the weighted least-squares solution (FIG. 8), the maximum likelihood solution (FIG. 9), and the exponential decay factor solution (FIG. 10) are combined to generate weighted variation correction coefficients at each sequencing cycle of the sequencing run.

Channel-Specific Offset Coefficients

FIG. 11 shows another implementation of determining the channel-specific offset coefficients. In the two-channel implementation, a first channel-specific offset coefficient ("Δx") for the first intensity channel and for the target cluster at the current sequencing cycle is calculated as a difference between the measured intensity ("p") in the first intensity channel for the target cluster at the current sequencing cycle and the intensity value ("u") in the first intensity channel at a centroid 1104 of a base-specific intensity distribution A 1102 to which the target cluster belongs at the current sequencing cycle (e.g., as determined by the expectation maximization algorithm).

In the two-channel implementation, a second channel-specific offset coefficient ("Δy") for the second intensity channel and for the target cluster at the current sequencing cycle is calculated as a difference between the measured intensity ("q") in the second intensity channel for the target cluster at the current sequencing cycle and the intensity value ("v") in the second intensity channel at the centroid 1104 of the base-specific intensity distribution A 1102 to which the target cluster belongs at the current sequencing cycle.

In one implementation, the first channel-specific offset coefficient ("Δx") and the second channel-specific offset coefficient ("Δy") are determined at each sequencing cycle of the sequencing run. In some implementations, after a configurable number of sequencing cycles (e.g., ten or twenty sequencing cycles), the first channel-specific offset coefficient ("Δx") and the second channel-specific offset coefficient ("Δy") are initialized with a predetermined value (e.g., "0").

In a rolling-average implementation, an average is calculated for the first offset channel-specific coefficient ("Δx")

and the second channel-specific offset coefficient ("Δy") after the configurable number of sequencing cycles. The average is then used as a substitute for the first offset channel-specific coefficient ("Δx") and the second channel-specific offset coefficient ("Δy") until the next average is calculated for the next set of the configurable number of sequencing cycles.

In some implementations, the first channel-specific offset coefficient ("Δx") and the second channel-specific offset coefficient ("Δy") are calculated only when the target cluster belongs to the A, C, and T base-specific intensity distributions, and not when the target cluster belongs to the G (dark) base-specific intensity distribution. In implementations when the sequencing run involves pair-ended reads, the first channel-specific offset coefficient ("Δx") and the second channel-specific offset coefficient ("Δy") are initialized for the second read with the values available at the end of the first read, but updated thereafter each set of the configurable number of sequencing cycles.

Performance Results

Figure 12:
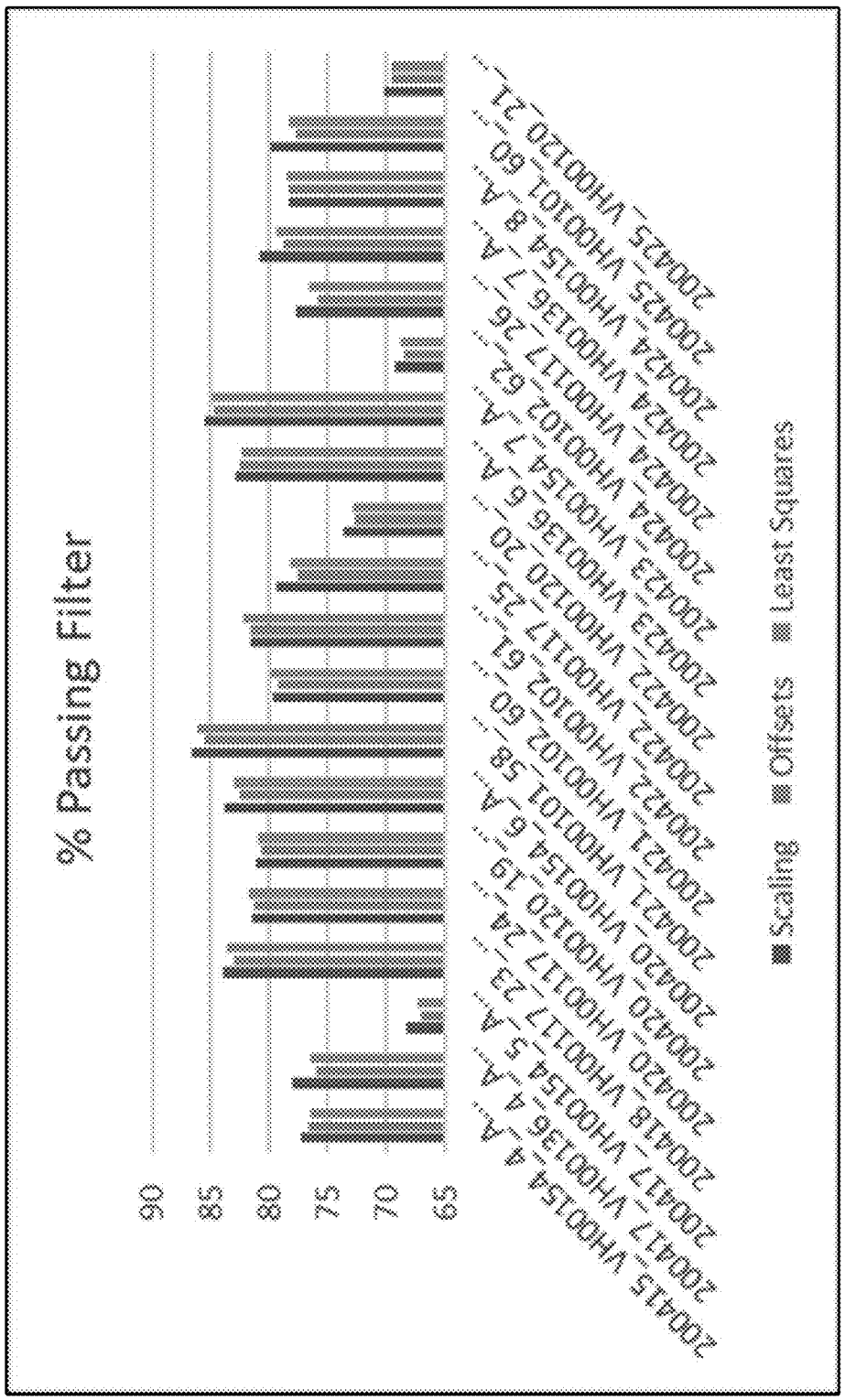
FIGS. 12, 13, and 14 compare performance of three approaches, namely, a scaling-only solution, an offsets-only solution (discussed in FIG. 11), and the least-squares solution (discussed in FIG. 3).
Figure 13:
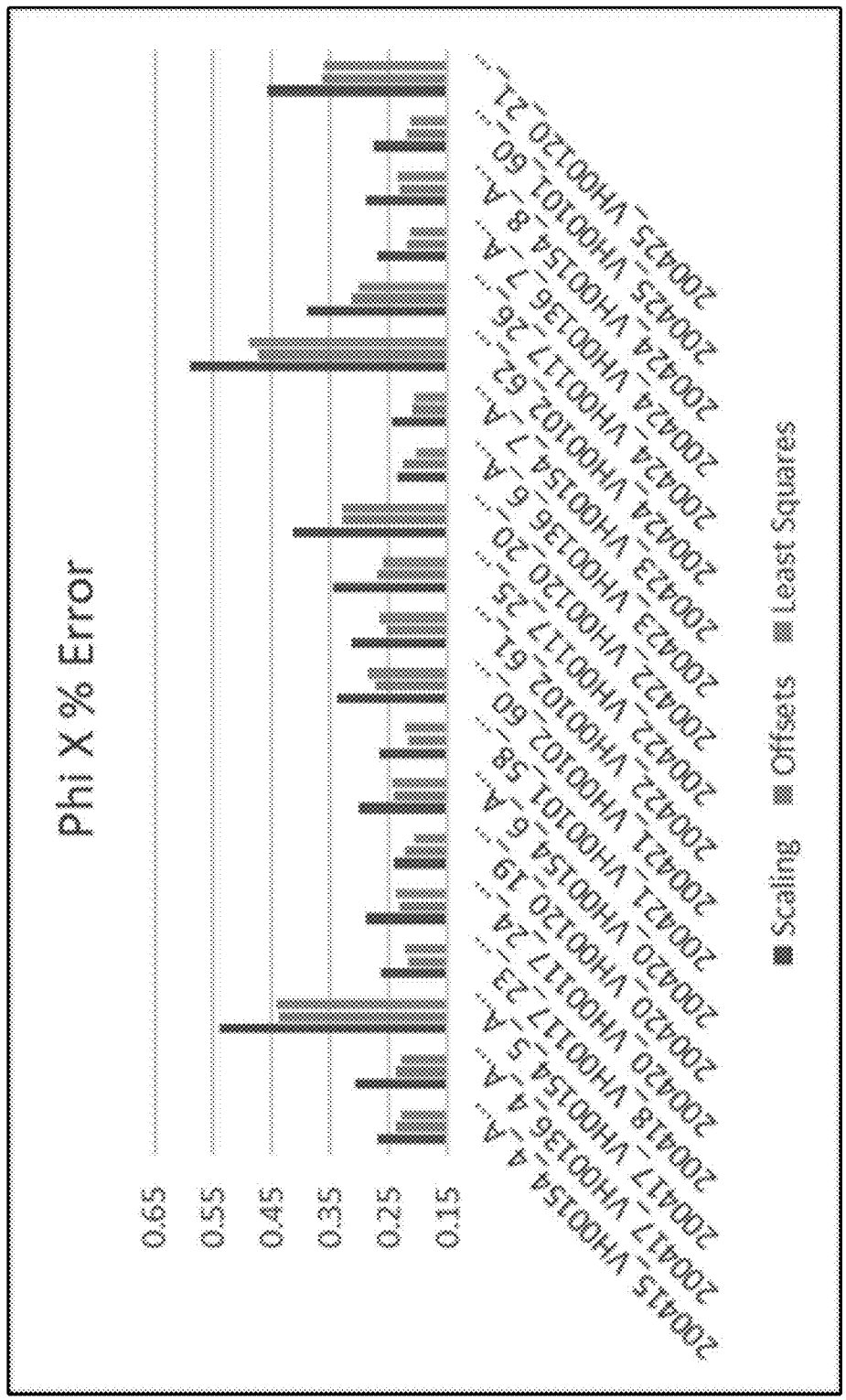
Figure 14:
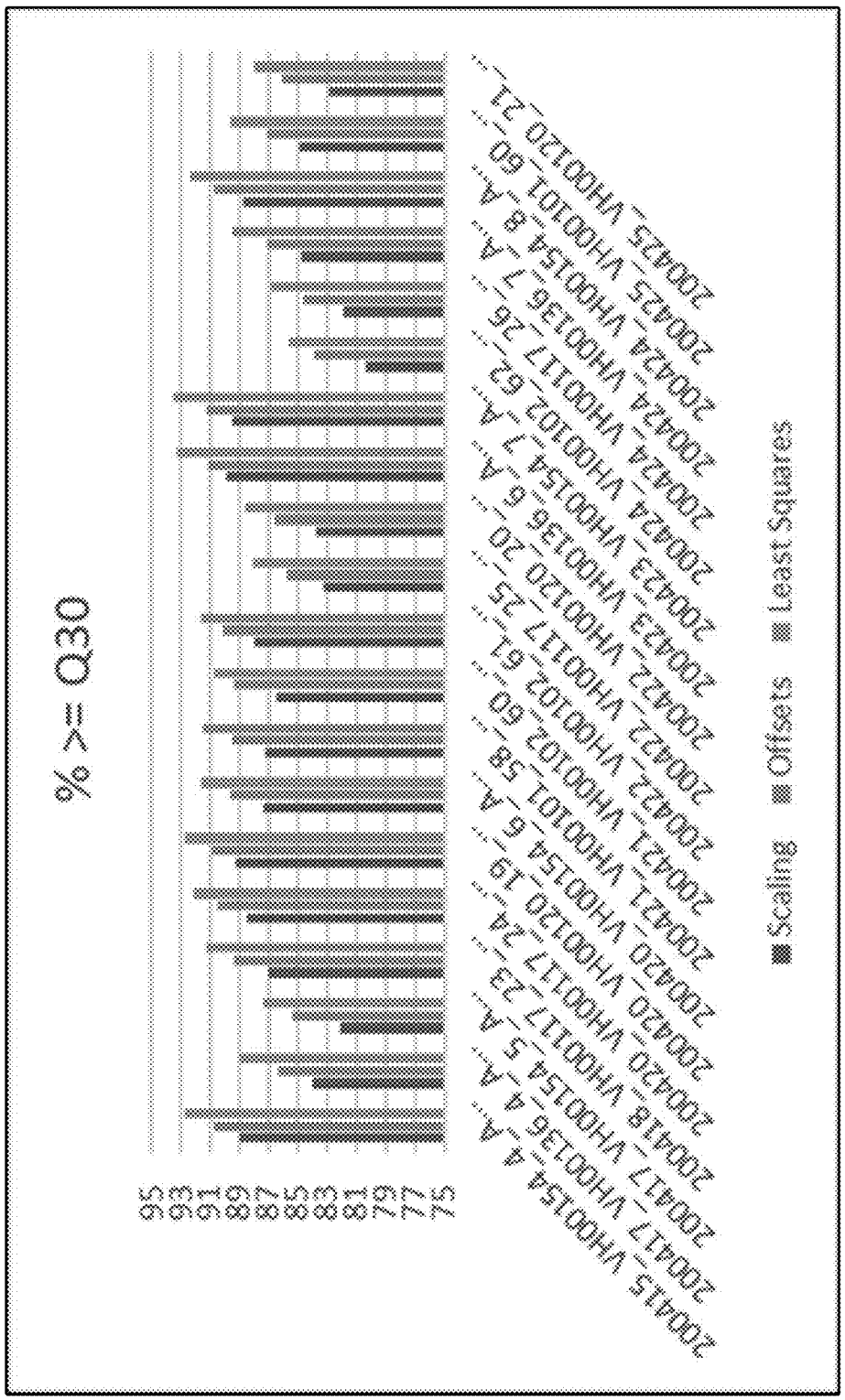

FIGS. 12, 13, and 14 compare performance of three approaches, namely, a scaling-only solution, an offsets-only solution (discussed in FIG. 11), and the least-squares solution 300. The three approaches are applied to intensity data generated using Illumina's Real-Time Analysis (RTA) software over twenty datasets from Illumina's sequencer Next-Seq 2000.

In FIG. 12, the performance of the scaling-only solution (left bar), the offsets-only solution (middle bar), and the least-squares solution (right bar) are comparatively plotted for the percentage of clusters passing the RTA's two-channel chastity filter. The comparison is done over the twenty datasets (shown as the x-axis). While all three approaches achieve >65% of clusters passing the two-channel chastity filter, 16 out of 20 cases (80%) score higher than 75% passing rate and 8/20 (or 20%) score >80% passing rate. Note that the least-squares solution 300 performs the best.

In FIG. 13, the performance of the scaling-only solution (left bar), the offsets-only solution (middle bar), and the least-squares solution (right bar) are comparatively plotted for the error rates in low-diversity samples. The comparison is done over twenty low-diversity datasets spiked with a known phage genome (PhiX) (shown as the x-axis). Seventeen out of twenty (17/20 or 68%) achieve <35% error rate, while majority enjoy lower than 25% error rates. Note that the least-squares solution 300 performs the best.

In FIG. 14, the performance of the scaling-only solution (left bar), the offsets-only solution (middle bar), and the least-squares solution (right bar) are comparatively plotted for the percentage of sequencing data have quality scores above Q30 (i.e. base call error<$10^{-30/10}$ or 0.1%). The comparison is done over the same twenty datasets (shown as the x-axis). While all three approaches enjoy high Q30 quality score (e.g. >80%), 16 out of 20 cases (80%) score higher than 75% passing rate and 8/20 (or 20%) score >80% passing rate. Note that the least-squares solution 300 outperforms the others by >2% points.

Computer System

Figure 15:
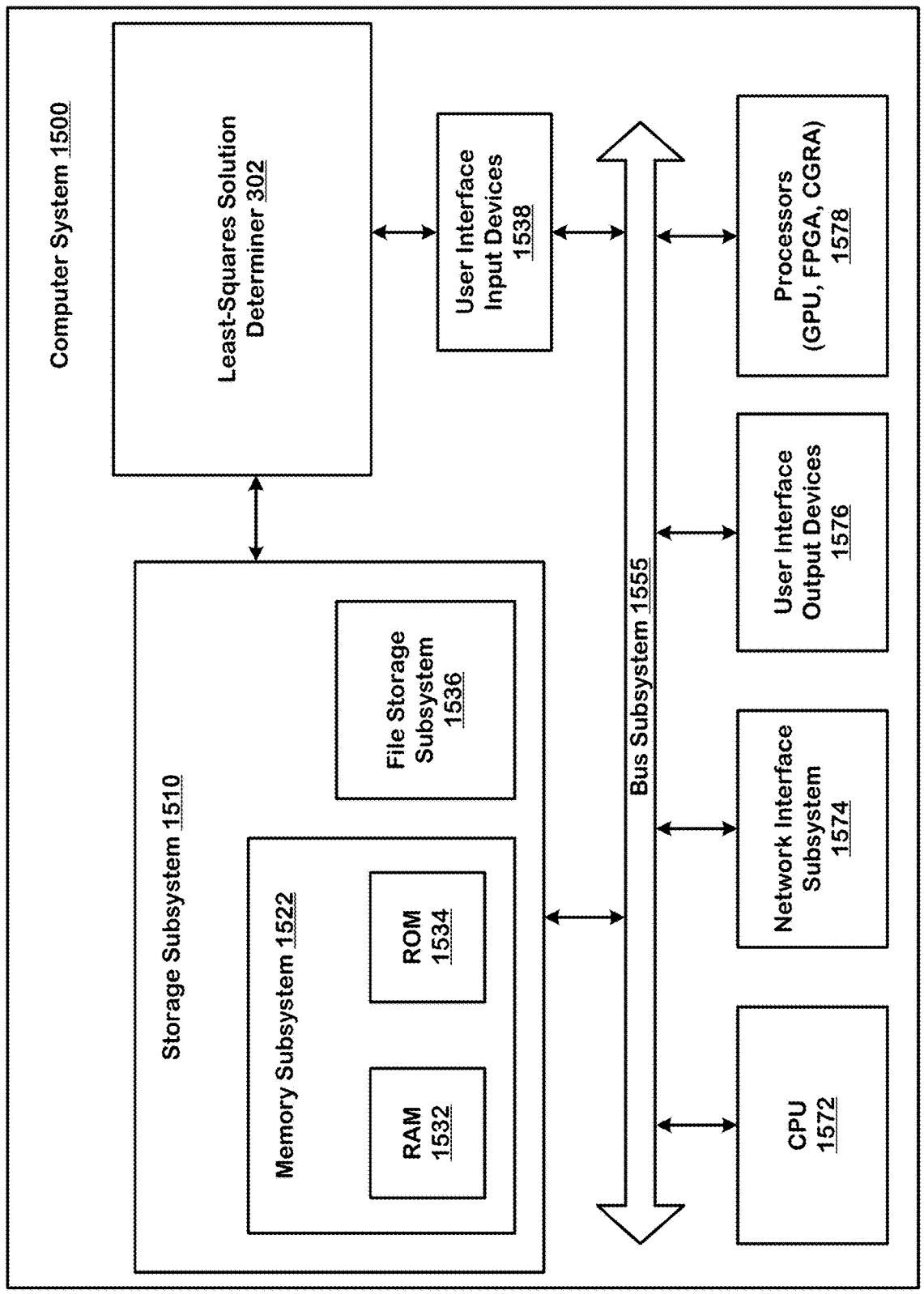
FIG. 15 is a computer system that can be used to implement the technology disclosed.

FIG. 15 is a computer system 1500 that can be used to implement the technology disclosed. Computer system 1500 includes at least one central processing unit (CPU) 1572 that communicates with a number of peripheral devices via bus subsystem 1555. These peripheral devices can include a storage subsystem 1510 including, for example, memory devices and a file storage subsystem 1536, user interface input devices 1538, user interface output devices 1576, and a network interface subsystem 1574. The input and output devices allow user interaction with computer system 1500. Network interface subsystem 1574 provides an interface to outside networks, including an interface to corresponding interface devices in other computer systems.

In one implementation, the least-squares solution determiner 302 is communicably linked to the storage subsystem 1510 and the user interface input devices 1538.

User interface input devices 1538 can include a keyboard; pointing devices such as a mouse, trackball, touchpad, or graphics tablet; a scanner; a touch screen incorporated into the display; audio input devices such as voice recognition systems and microphones; and other types of input devices. In general, use of the term "input device" is intended to include all possible types of devices and ways to input information into computer system 1500.

User interface output devices 1576 can include a display subsystem, a printer, a fax machine, or non-visual displays such as audio output devices. The display subsystem can include an LED display, a cathode ray tube (CRT), a flat-panel device such as a liquid crystal display (LCD), a projection device, or some other mechanism for creating a visible image. The display subsystem can also provide a non-visual display such as audio output devices. In general, use of the term "output device" is intended to include all possible types of devices and ways to output information from computer system 1500 to the user or to another machine or computer system.

Storage subsystem 1510 stores programming and data constructs that provide the functionality of some or all of the modules and methods described herein. These software modules are generally executed by processors 1578.

Processors 1578 can be graphics processing units (GPUs), field-programmable gate arrays (FPGAs), application-specific integrated circuits (ASICs), and/or coarse-grained reconfigurable architectures (CGRAs). Processors 1578 can be hosted by a deep learning cloud platform such as Google Cloud Platform™, Xilinx™, and Cirrascale™. Examples of processors 1578 include Google's Tensor Processing Unit (TPU)™, rackmount solutions like GX4 Rackmount Series™, GX15 Rackmount Series™, NVIDIA DGX-1™, Microsoft' Stratix V FPGA™, Graphcore's Intelligent Processor Unit (IPU)™, Qualcomm's Zeroth Platform™ with Snapdragon Processors™, NVIDIA's Volta™, NVIDIA's DRIVE PX™, NVIDIA's JETSON TX1/TX2 MODULE™, Intel's Nirvana™, Movidius VPU™, Fujitsu DPI™, ARM's DynamicIQ™, IBM TrueNorth™, Lambda GPU Server with Testa V100s™, and others.

Memory subsystem 1522 used in the storage subsystem 1510 can include a number of memories including a main random access memory (RAM) 1532 for storage of instructions and data during program execution and a read only memory (ROM) 1534 in which fixed instructions are stored. A file storage subsystem 1536 can provide persistent storage for program and data files, and can include a hard disk drive, a floppy disk drive along with associated removable media, a CD-ROM drive, an optical drive, or removable media cartridges. The modules implementing the functionality of certain implementations can be stored by file storage subsystem 1536 in the storage subsystem 1510, or in other machines accessible by the processor.

Bus subsystem 1555 provides a mechanism for letting the various components and subsystems of computer system 1500 communicate with each other as intended. Although bus subsystem 1555 is shown schematically as a single bus, alternative implementations of the bus subsystem can use multiple busses.

Computer system 1500 itself can be of varying types including a personal computer, a portable computer, a workstation, a computer terminal, a network computer, a television, a mainframe, a server farm, a widely-distributed set of loosely networked computers, or any other data processing system or user device. Due to the ever-changing nature of computers and networks, the description of computer system 1500 depicted in FIG. 15 is intended only as a specific example for purposes of illustrating the preferred implementations of the present invention. Many other configurations of computer system 1500 are possible having more or less components than the computer system depicted in FIG. 15.

Each of the processors or modules discussed herein may include an algorithm (e.g., instructions stored on a tangible and/or non-transitory computer readable storage medium) or sub-algorithms to perform particular processes. The variation corrector 232 is illustrated conceptually as a collection of modules, but may be implemented utilizing any combination of dedicated hardware boards, DSPs, processors, etc. Alternatively, the variation corrector 232 may be implemented utilizing an off-the-shelf PC with a single processor or multiple processors, with the functional operations distributed between the processors. As a further option, the modules described below may be implemented utilizing a hybrid configuration in which certain modular functions are performed utilizing dedicated hardware, while the remaining modular functions are performed utilizing an off-the-shelf PC and the like. The modules also may be implemented as software modules within a processing unit.

Various processes and steps of the methods set forth herein (e.g., FIG. 9) can be carried out using a computer. The computer can include a processor that is part of a detection device, networked with a detection device used to obtain the data that is processed by the computer or separate from the detection device. In some implementations, information (e.g., image data) may be transmitted between components of a system disclosed herein directly or via a computer network. A local area network (LAN) or wide area network (WAN) may be a corporate computing network, including access to the Internet, to which computers and computing devices comprising the system are connected. In one implementation, the LAN conforms to the transmission control protocol/internet protocol (TCP/IP) industry standard. In some instances, the information (e.g., image data) is input to a system disclosed herein via an input device (e.g., disk drive, compact disk player, USB port etc.). In some instances, the information is received by loading the information, e.g., from a storage device such as a disk or flash drive.

A processor that is used to run an algorithm or other process set forth herein may comprise a microprocessor. The microprocessor may be any conventional general purpose single- or multi-chip microprocessor such as a Pentium™ processor made by Intel Corporation. A particularly useful computer can utilize an Intel Ivybridge dual-12 core processor, LSI raid controller, having 128 GB of RAM, and 2 TB solid state disk drive. In addition, the processor may comprise any conventional special purpose processor such as a digital signal processor or a graphics processor. The processor typically has conventional address lines, conventional data lines, and one or more conventional control lines.

The implementations disclosed herein may be implemented as a method (e.g., FIGS. 2 and 7), apparatus, system or article of manufacture using standard programming or engineering techniques to produce software, firmware, hardware, or any combination thereof. The term "article of manufacture" as used herein refers to code or logic implemented in hardware or computer readable media such as optical storage devices, and volatile or non-volatile memory devices. Such hardware may include, but is not limited to, field programmable gate arrays (FPGAs), application-specific integrated circuits (ASICs), complex programmable logic devices (CPLDs), programmable logic arrays (PLAs), microprocessors, or other similar processing devices. In particular implementations, information or algorithms set forth herein are present in non-transient storage media.

In particular implementations, a computer-implemented method set forth herein (e.g., (discussed in FIG. 11)) can occur in real time while multiple images of an object are being obtained. Such real time analysis is particularly useful for nucleic acid sequencing applications wherein an array of nucleic acids is subjected to repeated cycles of fluidic and detection steps. Analysis of the sequencing data can often be computationally intensive such that it can be beneficial to perform the methods set forth herein in real time or in the background while other data acquisition or analysis algorithms are in process. Example real time analysis methods that can be used with the present methods are those used for the MiSeq and HiSeq sequencing devices commercially available from Illumina, Inc. (San Diego, Calif.) and/or described in US Pat. App. Pub. No. 2012/0020537 A1, which is incorporated herein by reference.

In this application, the terms "cluster", "well", "sample", "analyte," and "fluorescent sample" are interchangeable because a well contains a corresponding cluster/sample/analyte/fluorescent sample. As defined herein, "sample" and its derivatives, is used in its broadest sense and includes any specimen, culture and the like that is suspected of including a target. In some implementations, the sample comprises DNA, RNA, PNA, LNA, chimeric or hybrid forms of nucleic acids. The sample can include any biological, clinical, surgical, agricultural, atmospheric, or aquatic-based specimen containing one or more nucleic acids. The term also includes any isolated nucleic acid sample such a genomic DNA, fresh-frozen or formalin-fixed paraffin-embedded nucleic acid specimen. It is also envisioned that the sample can be from a single individual, a collection of nucleic acid samples from genetically related members, nucleic acid samples from genetically unrelated members, nucleic acid samples (matched) from a single individual such as a tumor sample and normal tissue sample, or sample from a single source that contains two distinct forms of genetic material such as maternal and fetal DNA obtained from a maternal subject, or the presence of contaminating bacterial DNA in a sample that contains plant or animal DNA. In some implementations, the source of nucleic acid material can include nucleic acids obtained from a newborn, for example as typically used for newborn screening.

The nucleic acid sample can include high molecular weight material such as genomic DNA (gDNA). The sample can include low molecular weight material such as nucleic acid molecules obtained from FFPE or archived DNA samples. In another implementation, low molecular weight material includes enzymatically or mechanically fragmented DNA. The sample can include cell-free circulating DNA. In some implementations, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some implementations, the sample can be an epidemiological, agricultural, forensic, or pathogenic sample. In some implementations, the sample can include nucleic acid molecules obtained from an animal such as a human or mammalian source. In another implementation, the sample can include nucleic acid molecules obtained from a non-mammalian source such as a plant, bacteria, virus, or fungus. In some implementations, the source of the nucleic acid molecules may be an archived or extinct sample or species.

Further, the methods and compositions disclosed herein may be useful to amplify a nucleic acid sample having low-quality nucleic acid molecules, such as degraded and/or fragmented genomic DNA from a forensic sample. In one implementation, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. The nucleic acid sample may be a purified sample or a crude DNA containing lysate, for example derived from a buccal swab, paper, fabric, or other substrate that may be impregnated with saliva, blood, or other bodily fluids. As such, in some implementations, the nucleic acid sample may comprise low amounts of, or fragmented portions of DNA, such as genomic DNA. In some implementations, target sequences can be present in one or more bodily fluids including but not limited to, blood, sputum, plasma, semen, urine, and serum. In some implementations, target sequences can be obtained from hair, skin, tissue samples, autopsy, or remains of a victim. In some implementations, nucleic acids including one or more target sequences can be obtained from a deceased animal or human. In some implementations, target sequences can include nucleic acids obtained from non-human DNA such a microbial, plant or entomological DNA. In some implementations, target sequences or amplified target sequences are directed to purposes of human identification. In some implementations, the disclosure relates generally to methods for identifying characteristics of a forensic sample. In some implementations, the disclosure relates generally to human identification methods using one or more target specific primers disclosed herein or one or more target specific primers designed using the primer design criteria outlined herein. In one implementation, a forensic or human identification sample containing at least one target sequence can be amplified using any one or more of the target-specific primers disclosed herein or using the primer criteria outlined herein.

The technology disclosed generates variation correction coefficients to correct inter-cluster intensity profile variation in image data. The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

Other implementations of the method described in this section can include a non-transitory computer readable storage medium storing instructions executable by a processor to perform any of the methods described above. Yet another implementation of the method described in this section can include a system including memory and one or more processors operable to execute instructions, stored in the memory, to perform any of the methods described above.

In another implementation, the variation correction is performed on non-intensity data, such as on pH changes induced by the release of hydrogen ions during molecule extension. The pH changes are detected and converted to a voltage change that is proportional to the number of bases incorporated (e.g., in the case of Ion Torrent).

In yet another implementation, the non-intensity data is constructed from nanopore sensing that uses biosensors to measure the disruption in current as an analyte passes through a nanopore or near its aperture while determining the identity of the base. For example, the Oxford Nanopore Technologies (ONT) sequencing is based on the following concept: pass a single strand of DNA (or RNA) through a membrane via a nanopore and apply a voltage difference across the membrane. The nucleotides present in the pore will affect the pore's electrical resistance, so current measurements over time can indicate the sequence of DNA bases passing through the pore. This electrical current signal (the 'squiggle' due to its appearance when plotted) is the raw data gathered by an ONT sequencer. These measurements are stored as 16-bit integer data acquisition (DAC) values, taken at 4 kHz frequency (for example). With a DNA strand velocity of ~450 base pairs per second, this gives approximately nine raw observations per base on average. This signal is then processed to identify breaks in the open pore signal corresponding to individual reads. These stretches of raw signal are base called—the process of converting DAC values into a sequence of DNA bases. In some implementations, the non-intensity data comprises normalized or scaled DAC values.

One or more implementations of the technology disclosed, or elements thereof can be implemented in the form of a computer product including a non-transitory computer readable storage medium with computer usable program code for performing the method steps indicated. Furthermore, one or more implementations of the technology disclosed, or elements thereof can be implemented in the form of an apparatus including a memory and at least one processor that is coupled to the memory and operative to perform exemplary method steps. Yet further, in another aspect, one or more implementations of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

This application uses the terms "accumulated intensity correction parameter(s)" and "intermediate term(s)" interchangeably.

This application uses the terms "pure intensity/intensities" and "distribution intensity/intensities" interchangeably.

This application uses the terms "intensity profile(s)" and "constellation(s)" interchangeably.

This application uses the terms "variation correction coefficient(s)" and "intensity correction coefficient(s)" interchangeably.

This application uses the terms "amplification coefficient" and "scaling factor" interchangeably.

This application uses the terms "offset coefficient(s)" and "offset(s)" interchangeably.

This application uses the terms "target cluster" and "particular cluster" interchangeably.

This application uses the terms "next," "subsequent," and "successive" interchangeably.

This application uses the terms "nucleotide(s)" and "base(s)" interchangeably.

This application uses the terms "accumulated intensity correction parameter determiner" and "accumulator" interchangeably.

This application uses the terms "accumulated intensity correction parameter determiner" and "accumulator" interchangeably.

Clauses

1. A computer-implemented method of base calling a target cluster, the method including:

for the target cluster, reading current channel-specific intensities registered for a current sequencing cycle of a sequencing run from a base-specific intensity distribution to which the target cluster is base called at the current sequencing cycle, reading current channel-specific distribution intensities from a centroid of the base-specific intensity distribution, determining a set of current intensity correction parameters for the current sequencing cycle based on the current channel-specific intensities and the current channel-specific distribution intensities, determining a set of current accumulated intensity correction parameters for the current sequencing cycle by accumulating the set of current intensity correction parameters and a set of preceding accumulated intensity correction parameters for a preceding sequencing cycle of the sequencing run, determining a current amplification coefficient and current channel-specific offset coefficients for the current sequencing cycle based on the set of current accumulated intensity correction parameters, and using the current amplification coefficient and the current channel-specific offset coefficients to correct next channel-specific intensities registered for a next sequencing cycle of the sequencing run and generate corrected next channel-specific intensities for the next sequencing cycle; and base calling the target cluster at the next sequencing cycle based on the corrected next channel-specific intensities.

2. The computer-implemented method of clause 1, wherein the set of current intensity correction parameters includes the current channel-specific distribution intensities, current channel-specific intensity errors, current distribution centroid-to-origin distance, and current distribution intensity-to-intensity error similarity measure.

3. The computer-implemented method of clause 2, wherein the current channel-specific intensity errors are channel-wise differences between the current channel-specific intensities and the current channel-specific distribution intensities.

4. The computer-implemented method of clause 2, wherein the current distribution centroid-to-origin distance is Euclidean distance between the centroid and an origin of a multi-dimensional space that contains the base-specific intensity distribution.

5. The computer-implemented method of clause 4, wherein the multi-dimensional space is at least one of a cartesian space, a polar space, a cylindrical space, and a spherical space.

6. The computer-implemented method of clause 2, wherein the current distribution intensity-to-intensity error similarity measure is a summation of channel-wise dot products between the current channel-specific distribution intensities and the current channel-specific intensity errors.

7. The computer-implemented method of clause 1, wherein the set of current accumulated intensity correction parameters are intensity correction parameter-wise sums of current intensity correction parameters in the set of current intensity correction parameters and preceding accumulated intensity correction parameters in the set of preceding accumulated intensity correction parameters.

8. The computer-implemented method of clause 7, wherein the set of current accumulated intensity correction parameters are intensity correction parameter-wise averages of the current intensity correction parameters and the preceding accumulated intensity correction parameters.

9. The computer-implemented method of clause 1, wherein the set of preceding accumulated intensity correction parameters and the set of current accumulated intensity correction parameters are stored in a quantized fixed bit width format.

10. The computer-implemented method of clause 1, wherein the current channel-specific offset coefficients are configured to be same.

11. The computer-implemented method of clause 10, wherein current accumulated intensity correction parameters in the set of current accumulated intensity correction parameters include a first common current accumulated intensity correction parameter for the current channel-specific distribution intensities, and a second common current accumulated intensity correction parameter for the current channel-specific intensity errors.

12. The computer-implemented method of clause 1, wherein the current channel-specific offset coefficients are channel-wise subtracted from the next channel-specific intensities to generate next channel-specific shifted intensities, and the next channel-specific shifted intensities are divided by the current amplification coefficient to generate the corrected next channel-specific intensities.

13. The computer-implemented method of clause 1, further including using a weighting function to combine an initial amplification coefficient with the current amplification coefficient, and initial channel-specific offset coefficients with the current channel-specific offset coefficients to generate a weighted current amplification coefficient and weighted current channel-specific offset coefficients for the current sequencing cycle.

14. The computer-implemented method of clause 13, wherein the weighting function applies a minimum weight ($w_{min}$) to initial amplification coefficient and the initial channel-specific offset coefficients, and a maximum weight ($w_{max}$) to the current amplification coefficient and the current channel-specific offset coefficients, wherein $w_{min}=(1-w_{max})$.

15. The computer-implemented method of clause 14, wherein the maximum weight ($w_{max}$) is defined as $(c-p)/c$, where c is an index for the current sequencing cycle and p is a number between 2 to 7.

16. The computer-implemented method of clause 15, further including using the weighted current amplification coefficient and the weighted current channel-specific offset coefficients to correct the next channel-specific intensities and generate the corrected next channel-specific intensities.

17. The computer-implemented method of clause 1, further including:

using a maximum likelihood solution to generate, for the current sequencing cycle, respective current maximum likelihood weights for the current amplification coefficient and the current channel-specific offset coefficients;

respectively applying the current maximum likelihood weights to the current amplification coefficient and the current channel-specific offset coefficients to generate a maximum likelihood weighted current amplification coefficient and maximum likelihood weighted current channel-specific offset coefficients for the current sequencing cycle; and using the maximum likelihood weighted current amplification coefficient and the maximum likelihood weighted current channel-specific offset coefficients to correct the next channel-specific intensities and generate the corrected next channel-specific intensities.

18. The computer-implemented method of clause 1, further including:

applying a decay factor to the current intensity correction parameters to generate decayed current intensity correction parameters for the current sequencing cycle; and determining the current accumulated intensity correction parameters by intensity correction parameter-wise accumulating the decayed current intensity correction parameters and the preceding accumulated intensity correction parameters.

19. The computer-implemented method of clause 18, wherein the decay factor is kept fixed for a certain number of sequencing cycles of the sequencing run, and exponentially decayed thereafter based on a decay logic.

20. The computer-implemented method of clause 19, wherein the decay logic is $1-1/tau$, where tau is a predefined number.

21. The computer-implemented method of clause 1, further including iterating the reading, the reading, the determining, the determining, the determining, the using, and the base calling for the target cluster at successive sequencing cycles of the sequencing run.

22. The computer-implemented method of clause 1, further including executing the reading, the reading, the determining, the determining, the determining, the using, and the base calling in parallel for multiple clusters.

23. The computer-implemented method of clause 1, wherein closed-form expressions for the set of current intensity correction parameters, the set of current accumulated intensity correction parameters, the current amplification coefficient, and the current channel-specific offset coefficients are determined using a least-squares solution.

24. The computer-implemented method of clause 1, wherein the current channel-specific intensities respectively correspond to intensity channels.

25. The computer-implemented method of clause 1, wherein the current channel-specific offset coefficients are the channel-wise differences between the current channel-specific intensities and the current channel-specific distribution intensities.

26. A non-transitory computer readable storage medium impressed with computer program instructions to base call a target cluster, the instructions, when executed on a processor, implement a method comprising:

for the target cluster, reading current channel-specific intensities registered for a current sequencing cycle of a sequencing run from a base-specific intensity distribution to which the target cluster is base called at the current sequencing cycle, reading current channel-specific distribution intensities from a centroid of the base-specific intensity distribution, determining a set of current intensity correction parameters for the current sequencing cycle based on the current channel-specific intensities and the current channel-specific distribution intensities, determining a set of current accumulated intensity correction parameters for the current sequencing cycle by accumulating the set of current intensity correction parameters and a set of preceding accumulated intensity correction parameters for a preceding sequencing cycle of the sequencing run, determining a current amplification coefficient and current channel-specific offset coefficients for the current sequencing cycle based on the set of current accumulated intensity correction parameters, and using the current amplification coefficient and the current channel-specific offset coefficients to correct next channel-specific intensities registered for a next sequencing cycle of the sequencing run and generate corrected next channel-specific intensities for the next sequencing cycle; and base calling the target cluster at the next sequencing cycle based on the corrected next channel-specific intensities.

27. The non-transitory computer readable storage medium of clause 26, implementing each clause that ultimately depends on clause 1.

28. A system including one or more processors coupled to memory, the memory loaded with computer instructions to base call a target cluster, the instructions, when executed on the processors, implement actions comprising:

for the target cluster, reading current channel-specific intensities registered for a current sequencing cycle of a sequencing run from a base-specific intensity distribution to which the target cluster is base called at the current sequencing cycle, reading current channel-specific distribution intensities from a centroid of the base-specific intensity distribution, determining a set of current intensity correction parameters for the current sequencing cycle based on the current channel-specific intensities and the current channel-specific distribution intensities, determining a set of current accumulated intensity correction parameters for the current sequencing cycle by accumulating the set of current intensity correction parameters and a set of preceding accumulated intensity correction parameters for a preceding sequencing cycle of the sequencing run, determining a current amplification coefficient and current channel-specific offset coefficients for the current sequencing cycle based on the set of current accumulated intensity correction parameters, and using the current amplification coefficient and the current channel-specific offset coefficients to correct next channel-specific intensities registered for a next sequencing cycle of the sequencing run and generate corrected next channel-specific intensities for the next sequencing cycle; and base calling the target cluster at the next sequencing cycle based on the corrected next channel-specific intensities.

29. The system of clause 28, implementing each clause that ultimately depends on clause 1.

30. A computer-implemented method of base calling a target cluster, the method including:

for the target cluster,
accessing current intensity data and historic intensity data,
wherein the current intensity data is for a current sequencing cycle of a sequencing run, and
wherein the historic intensity data is for one or more preceding sequencing cycles of the sequencing run,
determining a scale correction coefficient and channel-specific shift correction coefficients based on the current intensity data and the historic intensity data,
using the scale correction coefficient and the channel-specific shift correction coefficients to correct next intensity data and generate corrected next intensity data,
wherein the next intensity data is for a next sequencing cycle of the sequencing run; and
base calling the target cluster at the next sequencing cycle based on the corrected next intensity data.

31. The computer-implemented method of clause 30, implementing each clause that ultimately depends on clause 1.

32. A non-transitory computer readable storage medium impressed with computer program instructions to base call a target cluster, the instructions, when executed on a processor, implement a method comprising:
for the target cluster,
accessing current intensity data and historic intensity data,
wherein the current intensity data is for a current sequencing cycle of a sequencing run, and
wherein the historic intensity data is for one or more preceding sequencing cycles of the sequencing run,
determining a scale correction coefficient and channel-specific shift correction coefficients based on the current intensity data and the historic intensity data,
using the scale correction coefficient and the channel-specific shift correction coefficients to correct next intensity data and generate corrected next intensity data,
wherein the next intensity data is for a next sequencing cycle of the sequencing run; and
base calling the target cluster at the next sequencing cycle based on the corrected next intensity data.

33. The non-transitory computer readable storage medium of clause 32, implementing each clause that ultimately depends on clause 1.

34. A system including one or more processors coupled to memory, the memory loaded with computer instructions to base call a target cluster, the instructions, when executed on the processors, implement actions comprising:
for the target cluster,
accessing current intensity data and historic intensity data,
wherein the current intensity data is for a current sequencing cycle of a sequencing run, and
wherein the historic intensity data is for one or more preceding sequencing cycles of the sequencing run,
determining a scale correction coefficient and channel-specific shift correction coefficients based on the current intensity data and the historic intensity data,
using the scale correction coefficient and the channel-specific shift correction coefficients to correct next intensity data and generate corrected next intensity data,
wherein the next intensity data is for a next sequencing cycle of the sequencing run; and
base calling the target cluster at the next sequencing cycle based on the corrected next intensity data.

35. The system of clause 34, implementing each clause that ultimately depends on clause 1.

36. A computer-implemented method of base calling a target cluster, the method including:
for the target cluster,
accessing current intensity data and historic intensity data,
wherein the current intensity data is for a current sequencing cycle of a sequencing run, and
wherein the historic intensity data is for one or more preceding sequencing cycles of the sequencing run,
using the current intensity data and the historic intensity data to correct next intensity data and generate corrected next intensity data,
wherein the next intensity data is for a next sequencing cycle of the sequencing run; and
base calling the target cluster at the next sequencing cycle based on the corrected next intensity data.

37. The computer-implemented method of clause 36, implementing each clause that ultimately depends on clause 1.

38. A non-transitory computer readable storage medium impressed with computer program instructions to base call a target cluster, the instructions, when executed on a processor, implement a method comprising:
for the target cluster,
accessing current intensity data and historic intensity data,
wherein the current intensity data is for a current sequencing cycle of a sequencing run, and
wherein the historic intensity data is for one or more preceding sequencing cycles of the sequencing run,
using the current intensity data and the historic intensity data to correct next intensity data and generate corrected next intensity data,
wherein the next intensity data is for a next sequencing cycle of the sequencing run; and
base calling the target cluster at the next sequencing cycle based on the corrected next intensity data.

39. The non-transitory computer readable storage medium of clause 38, implementing each clause that ultimately depends on clause 1.

40. A system including one or more processors coupled to memory, the memory loaded with computer instructions to base call a target cluster, the instructions, when executed on the processors, implement actions comprising:
for the target cluster,
accessing current intensity data and historic intensity data,
wherein the current intensity data is for a current sequencing cycle of a sequencing run, and
wherein the historic intensity data is for one or more preceding sequencing cycles of the sequencing run,
using the current intensity data and the historic intensity data to correct next intensity data and generate corrected next intensity data,
wherein the next intensity data is for a next sequencing cycle of the sequencing run; and
base calling the target cluster at the next sequencing cycle based on the corrected next intensity data.

41. The system of clause 40, implementing each clause that ultimately depends on clause 1.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A system comprising at least one processor coupled to memory, the memory loaded with computer instructions that, when executed by the at least one processor, implement actions comprising:
   accessing, for a target cluster, current intensities registered from the target cluster and other clusters for a current sequencing cycle;
   determining a set of current accumulated intensity correction parameters for the current sequencing cycle based on the current intensities;
   determining, for the target cluster and based on the set of current accumulated intensity correction parameters, a current amplification coefficient;
   correcting next intensities registered for a next sequencing cycle based on the current amplification coefficient; and
   determining a base call for the target cluster at the next sequencing cycle based on the corrected next intensities.

2. The system of claim 1, further comprising computer instructions that, when executed by the at least one processor, implement actions comprising:
   accessing, for the target cluster, current distribution intensities from a base-specific intensity distribution; and
   determining the set of current accumulated intensity correction parameters for the current sequencing cycle further based on the current distribution intensities.

3. The system of claim 2, wherein:
   the current intensities comprise current channel-specific intensities registered for the current sequencing cycle; and
   the current distribution intensities comprise current channel-specific distribution intensities from the base-specific intensity distribution.

4. The system of claim 1, wherein the current amplification coefficient scales the current intensities for the target cluster relative to intensities of the other clusters on a flow cell.

5. The system of claim 1, wherein the current amplification coefficient scales the current intensities for the target cluster relative to channel-specific intensities or cluster-specific intensities of the other clusters on a flow cell.

6. The system of claim 1, further comprising computer instructions that, when executed by the at least one processor, implement actions comprising:
   combining an initial amplification coefficient with the current amplification coefficient to generate a modified current amplification coefficient; and
   correcting the next intensities registered for the next sequencing cycle based on the modified current amplification coefficient.

7. The system of claim 6, further comprising computer instructions that, when executed by the at least one processor, implement actions comprising combining the initial amplification coefficient with the current amplification coefficient to generate the modified current amplification coefficient by:
   applying, utilizing a weighting function, a first weight to the initial amplification coefficient;
   applying, utilizing the weighting function, a second weight to the current amplification coefficient; and
   generating a weighted current amplification coefficient based on the first weighted initial amplification coefficient and the second weighted current amplification coefficient.

8. The system of claim 6, further comprising computer instructions that, when executed by the at least one processor, implement actions comprising combining the initial amplification coefficient with the current amplification coefficient to generate the modified current amplification coefficient by:
   applying, utilizing a weighting function, a minimum weight ($w_{min}$) to the initial amplification coefficient;
   applying, utilizing the weighting function, a maximum weight ($w_{max}$) to the current amplification coefficient; and
   generating a weighted current amplification coefficient based on the minimum weighted initial amplification coefficient and the maximum weighted current amplification coefficient.

9. The system of claim 1, further comprising computer instructions that, when executed by the at least one processor, implement actions comprising:
   determining offset coefficients that offset cluster-specific intensity for the current sequencing cycle based on the set of current accumulated intensity correction parameters; and
   correcting, for the next sequencing cycle, the next intensities registered based on the current amplification coefficient and the offset coefficients.

10. The system of claim 1, further comprising computer instructions that, when executed by the at least one processor, implement actions comprising correcting the next intensities by correcting, for the next sequencing cycle, the next intensities for inter-cluster intensity variation among intensity values from different clusters for respective bases.

11. A non-transitory computer readable storage medium storing computer instructions that, when executed by at least one processor, cause a system to:
   access, for a target cluster, current intensities registered from the target cluster and other clusters for a current sequencing cycle;
   determine a set of current accumulated intensity correction parameters for the current sequencing cycle based on the current intensities;
   determine, for the target cluster and based on the set of current accumulated intensity correction parameters, a current amplification coefficient;
   correct next intensities registered for a next sequencing cycle based on the current amplification coefficient; and
   determine a base call for the target cluster at the next sequencing cycle based on the corrected next intensities.

12. The non-transitory computer readable storage medium of claim 11, further storing computer instructions that, when executed by the at least one processor, cause the system to:
   access, for the target cluster, current distribution intensities from a base-specific intensity distribution; and
   determine the set of current accumulated intensity correction parameters for the current sequencing cycle further based on the current distribution intensities.

13. The non-transitory computer readable storage medium of claim 11, wherein the current amplification coefficient scales the current intensities for the target cluster relative to intensities of the other clusters on a flow cell.

14. The non-transitory computer readable storage medium of claim 11, wherein the current amplification coefficient scales the current intensities for the target cluster relative to channel-specific intensities or cluster-specific intensities of the other clusters on a flow cell.

15. The non-transitory computer readable storage medium of claim 11, further storing computer instructions that, when executed by the at least one processor, cause the system to:
combine an initial amplification coefficient with the current amplification coefficient to generate a modified current amplification coefficient; and
correct the next intensities registered for the next sequencing cycle based on the modified current amplification coefficient.

16. The non-transitory computer readable storage medium of claim 15, further storing computer instructions that, when executed by the at least one processor, cause the system to combine the initial amplification coefficient with the current amplification coefficient to generate the modified current amplification coefficient by:
applying, utilizing a weighting function, a first weight to the initial amplification coefficient;
applying, utilizing the weighting function, a second weight to the current amplification coefficient; and
generating a weighted current amplification coefficient based on the first weighted initial amplification coefficient and the second weighted current amplification coefficient.

17. The non-transitory computer readable storage medium of claim 15, further storing computer instructions that, when executed by the at least one processor, cause the system to combine the initial amplification coefficient with the current amplification coefficient to generate the modified current amplification coefficient by:
applying, utilizing a weighting function, a minimum weight ($w_{min}$) to the initial amplification coefficient;
applying, utilizing the weighting function, a maximum weight ($w_{max}$) to the current amplification coefficient; and
generating a weighted current amplification coefficient based on the minimum weighted initial amplification coefficient and the maximum weighted current amplification coefficient.

18. A computer-implemented method comprising:
accessing, for a target cluster, current intensities registered from the target cluster and other clusters for a current sequencing cycle;
determining a set of current accumulated intensity correction parameters for the current sequencing cycle based on the current intensities;
determining, for the target cluster and based on the set of current accumulated intensity correction parameters, a current amplification coefficient;
correcting next intensities registered for a next sequencing cycle based on the current amplification coefficient; and
determining a base call for the target cluster at the next sequencing cycle based on the corrected next intensities.

19. The computer-implemented method of claim 18, further comprising:
determining offset coefficients that offset cluster-specific intensity for the current sequencing cycle based on the set of current accumulated intensity correction parameters; and
correcting, for the next sequencing cycle, the next intensities registered based on the current amplification coefficient and the offset coefficients.

20. The computer-implemented method of claim 18, wherein correcting the next intensities comprises correcting, for the next sequencing cycle, the next intensities for inter-cluster intensity variation among intensity values from different clusters for respective bases.

* * * * *